(12) United States Patent
Yoo et al.

(10) Patent No.: US 10,926,128 B2
(45) Date of Patent: Feb. 23, 2021

(54) EXCERCISE GUIDE SYSTEM AND EXERCISE MANAGEMENT METHOD ACCORDING THERETO

(71) Applicant: DRAX INC., Anyang-si (KR)

(72) Inventors: Seon Kyung Yoo, Seoul (KR); Jae Sang Park, Seongnam-si (KR)

(73) Assignee: DRAX Inc., Gyeonggi-do (KR)

( * ) Notice: Subject to any disclaimer, the term of this patent is extended or adjusted under 35 U.S.C. 154(b) by 1 day.

(21) Appl. No.: 16/206,847

(22) PCT Filed: May 31, 2017

(86) PCT No.: PCT/KR2017/005660
§ 371 (c)(1),
(2) Date: Nov. 30, 2018

(87) PCT Pub. No.: WO2017/209500
PCT Pub. Date: Dec. 7, 2017

(65) Prior Publication Data
US 2019/0224520 A1 Jul. 25, 2019

(30) Foreign Application Priority Data
May 31, 2016 (KR) .................. 10-2016-0067746

(51) Int. Cl.
*A63B 22/02* (2006.01)
*A63B 71/06* (2006.01)
*A63B 24/00* (2006.01)

(52) U.S. Cl.
CPC .............. *A63B 22/02* (2013.01); *A63B 24/00* (2013.01); *A63B 24/0062* (2013.01);
(Continued)

(58) Field of Classification Search
CPC ....... A63B 22/025; A63B 24/00; A63B 22/02; A63B 71/06; A63B 24/0062;
(Continued)

(56) References Cited

U.S. PATENT DOCUMENTS 5,368,532 A * 11/1994 Farnet .................... A63B 22/02
482/5
2012/0010048 A1 1/2012 Bayerlein et al.
2016/0144225 A1* 5/2016 Dalebout ........... A63B 22/0285
482/54
(Continued)

FOREIGN PATENT DOCUMENTS

KR 10-0413703 B1 1/2004
KR 10-1345798 B1 12/2013
(Continued)

OTHER PUBLICATIONS

Notice of Allowance of corresponding Korean Patent Application No. 10-2018-0079428—7 pages (dated Jul. 17, 2019).
(Continued)

*Primary Examiner* — Sundhara M Ganesan
(74) *Attorney, Agent, or Firm* — Knobbe Martens Olson & Bear LLP

(57) ABSTRACT

Provided is an exercise guide system. The exercise guide system guides a user in an exercise on a treadmill, of which the speed is controllable according to the user's free will. The exercise guide system includes an input unit configured to receive at least one target exercise speed, a detection unit configured to detect an actual exercise speed of the user on the treadmill. The exercise guide system further includes an exercise guide unit configured to provide information related to the actual exercise speed and the target exercise speed so that the user personally adjusts an exercise speed on the treadmill.

9 Claims, 20 Drawing Sheets

(52) U.S. Cl.
CPC .......... *A63B 24/0075* (2013.01); *A63B 71/06* (2013.01); *A63B 71/0622* (2013.01); *A63B 22/025* (2015.10); *A63B 2024/0068* (2013.01); *A63B 2071/0625* (2013.01); *A63B 2071/0655* (2013.01); *A63B 2220/30* (2013.01); *A63B 2220/62* (2013.01); *A63B 2225/50* (2013.01); *A63B 2230/06* (2013.01); *A63B 2230/50* (2013.01)

(58) Field of Classification Search
CPC ............ A63B 24/0075; A63B 71/0622; A63B 2024/0068; A63B 2071/0625; A63B 2071/0655; A63B 2220/30; A63B 2220/62; A63B 2225/50; A63B 2230/06; A63B 2230/50; A63B 24/0087; A63B 71/0054; A63B 2220/34; A63B 2220/833; A63B 71/0669; A63B 2071/0675; A63B 2225/20; A63B 2071/0694; A63B 24/0006; A63B 2024/0093; A63B 71/0619; A63B 22/0242; A63B 2230/04; H04W 4/00; H04W 4/025; H04W 4/80; G06Q 50/22; G06Q 50/10; G16H 50/30; G16H 20/30
See application file for complete search history.

(56) References Cited

U.S. PATENT DOCUMENTS

2016/0367851 A1* 12/2016 Astilean .................. B62K 7/00
2017/0136298 A1*  5/2017 Bae .................... A63B 24/0062

FOREIGN PATENT DOCUMENTS

| KR | 10-1379666 B1 | 4/2014 |
| KR | 10-1495501 B1 | 3/2015 |
| KR | 10-1518486 B1 | 5/2015 |
| KR | 10-2015-0064506 A | 6/2015 |

OTHER PUBLICATIONS

Decision of Rejection of corresponding Korean Patent Application No. 10-2018-0079428—4 pages (dated Apr. 19, 2019).
Decision of Rejection of corresponding Korean Patent Application No. 10-2016-0067746—3 pages (dated May 8, 2018).
Office Action of corresponding Korean Patent Application No. 10-2016-0067746—6 pages (dated Nov. 9, 2017).
International Search Report and Written Opinion dated Aug. 30, 2017 in corresponding International Application No. PCT/KR2017/005660.

\* cited by examiner

EXCERCISE GUIDE SYSTEM AND EXERCISE MANAGEMENT METHOD ACCORDING THERETO

CROSS-REFERENCE TO RELATED APPLICATIONS

This application is a continuation application, and claims the benefit under 35 U.S.C. §§ 120 and 365 of PCT Application No. PCT/KR2017/005660, filed on May 31, 2017, which is hereby incorporated by reference. PCT/KR2017/005660 also claimed priority from Korean Patent Application No. 10-2016-0067746 filed on May 31, 2016 which is hereby incorporated by reference.

BACKGROUND

The present disclosure relates to an exercise guide system and an exercise management method according thereto.

A treadmill is an exercise machine that gives the effect of a walking or running exercise in a small space using a belt rotating along an infinite orbit, and is also called a running machine. Demands for treadmills are ever increasing because treadmills allow users to walk or run indoors at proper temperatures, regardless of the weather.

Treadmills may be classified into automatic treadmills, in which a track part is rotated by a separate driving means, and manual treadmills, in which a track part is rotated by a user without a separate driving means.

Automatic treadmills usually include a motor which is a separate driving means for rotating a track belt. In such automatic treadmills, a user controls the rotation speed of the motor by controlling a speed button, and the user's exercise speed is controlled according thereto. Automatic treadmills may allow a user to exercise at a constant speed via the rotation of a motor but may cause injury to the user when the user does not keep up with a target exercise speed.

Contrarily, manual treadmills have a structure in which a track part is rotated by a user's leg motion without a separate driving means. Since the speed of manual treadmills is controlled according to the free will of a user, manual treadmills may prevent injury. However, due to the structural characteristics of manual treadmills, a user has difficulty in exercising according to the goal of exercise.

SUMMARY

Provided are an exercise guide system for guiding a user on a treadmill of which the speed is controllable according to the free will of the user, thereby enabling the user to exercise at a target exercise speed, and an exercise management method according thereto.

According to an aspect of the present disclosure, an exercise guide system guides a user in an exercise on a treadmill of which the speed is controllable according to the user's free will, and the exercise guide system includes: an input unit configured to receive at least one target exercise speed; a detection unit configured to detect an actual exercise speed of the user on the treadmill; and an exercise guide unit configured to provide information related to the actual exercise speed and the target exercise speed so that the user personally adjusts an exercise speed on the treadmill.

In an embodiment, the information provided by the exercise guide unit may be information related to a difference between the actual exercise speed and the target exercise speed.

In an embodiment, the exercise guide unit may be configured to provide the user with the information related to the difference between the actual exercise speed and the target exercise speed when the difference between the actual exercise speed and the target exercise speed is beyond a certain error range.

In an embodiment, the exercise guide unit may be configured to score the difference between the actual exercise speed and the target exercise speed and to provide a score for the user.

In an embodiment, the exercise guide unit may be configured to provide the information using at least one of visual sense, auditory sense, and tactile sense.

In an embodiment, the exercise guide system may further include a communication unit configured to transmitting the information provided by the exercise guide unit to outside the exercise guide system.

In an embodiment, the actual exercise speed on the treadmill may be adjusted by the user's leg motion.

In an embodiment, the actual exercise speed may be variable.

In an embodiment, the input unit may be configured to receive a target heart rate of the user, the detection unit may be configured to detect an actual heart rate of the user, and the exercise guide unit may be configured to provide information related to the actual heart rate and the target heart rate.

According to another aspect of the present disclosure, an exercise guide system guides a user in an exercise on an exercise machine, and the exercise guide system includes: an input unit configured to input a target exercise item; a detection unit configured to detect an actual exercise item of the user on the exercise machine; and an exercise guide unit configured to provide information related to a difference between the actual exercise item and the target exercise item so that the user personally adjusts an exercise item on the exercise machine.

In an embodiment, the exercise item may be at least one of an exercise speed, a heart rate, and a body temperature.

In an embodiment, the actual exercise item of the user may be variable.

According to a further aspect of the present disclosure, an exercise management method is an exercise management method according to an exercise guide system which guides a user in an exercise on a treadmill, of which the speed is controllable according to the user's free will, and the exercise management method includes: receiving a target exercise speed; detecting an actual exercise speed of the user on the treadmill; and providing the user with information related to the actual exercise speed and the target exercise speed, wherein an exercise speed of the user on the treadmill is adjusted according to a positional movement of the user based on the information.

Other aspects, features, and advantages than those described above will be clear from the accompanying drawings, the claims, and the description of embodiments below.

These general and specific aspects may be embodied using a system, a method, a computer program, or a combination thereof.

As described above, according to the present disclosure, an exercise guide system and an exercise management method provide a user with information related to an actual exercise speed and a target exercise speed, thereby guiding the user so that the user can exercise at a target exercise speed on a treadmill of which the speed is controllable according to the tree will of the user.

DETAILED DESCRIPTION

The configuration of an embodiment of the present disclosure will be described in detail with reference to the accompanying drawings. In describing the present disclosure, the detailed descriptions of the known functions or configurations will be omitted to make the gist of the present disclosure clear.

Figure 1:
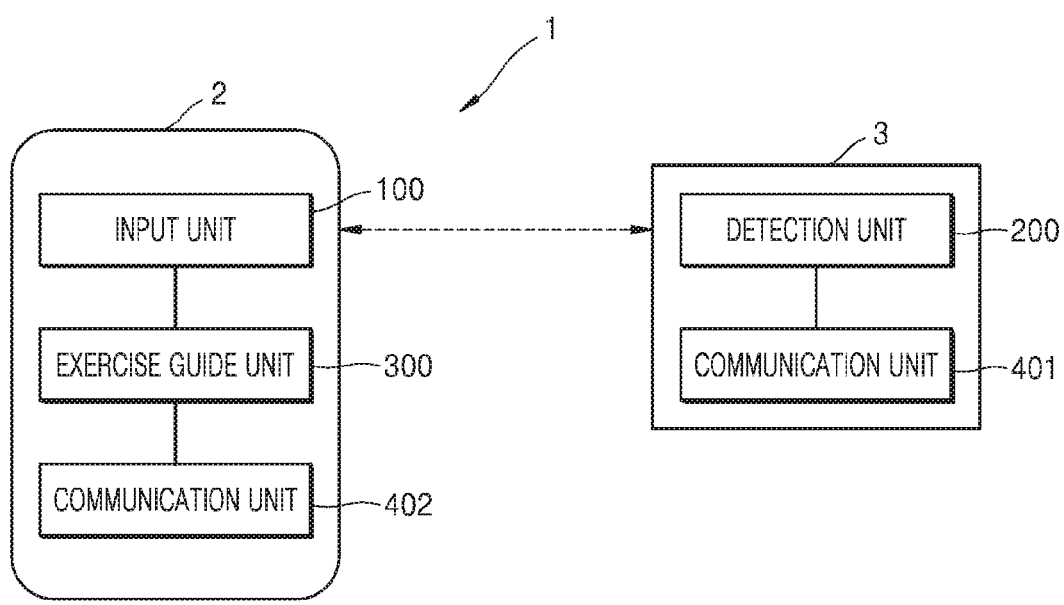
FIG. 1 is a diagram of the configuration of an exercise guide system according to an embodiment.
Figure 2:
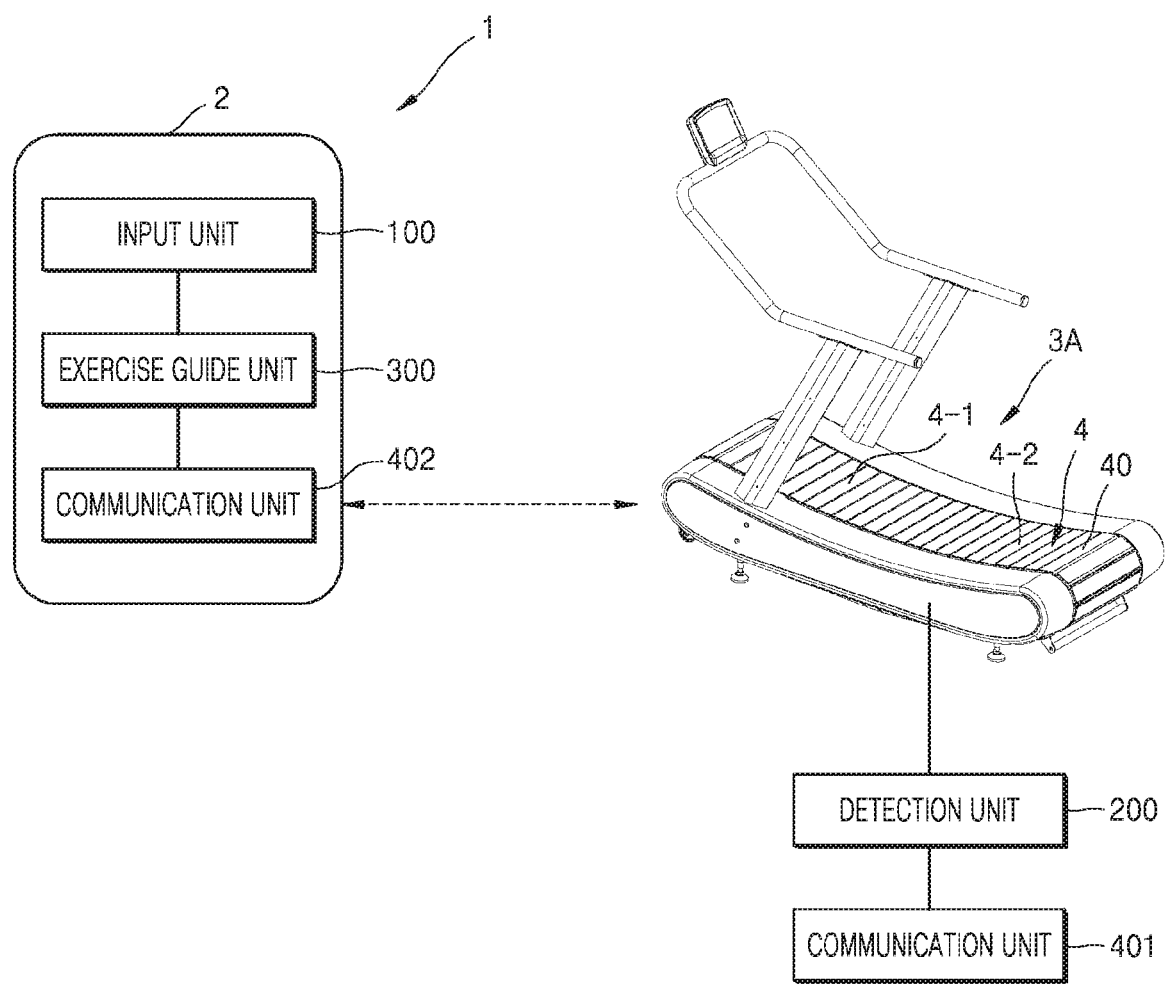
FIG. 2 is a diagram for explaining an example of the configuration of an exercise guide system, according to an embodiment.

FIG. 1 is a diagram of the configuration of an exercise guide system 1 according to an embodiment. FIG. 2 is a diagram for explaining an example of the configuration of the exercise guide system 1, according to an embodiment.

Referring to FIG. 1, the exercise guide system 1 includes an input unit 100 for inputting a target exercise item of a user, a detection unit 200 detecting an actual exercise item of the user in an exercise machine 3, and an exercise guide unit 300 providing the user with exercise information so that the user may control an exercise item.

Referring to FIGS. 1 and 2, the exercise machine 3 may be a treadmill 3A. For example, the exercise machine 3 may be the treadmill 3A of which the speed may be controlled according to the free will of a user. For example, the treadmill 3A may be configured such that a speed may be controlled without a separate hand movement, such as pressing a button, for speed control.

In an embodiment, the treadmill 3A may be a manual treadmill that rotates via a user's leg motion. For example, the treadmill 3A may be a manual treadmill in which a track part 4 that rotates has a curved shape. The track part 4 may includes a plurality of slats 40.

In another embodiment, the treadmill 3A may be an automatic treadmill, in which rotation is performed by a motor but a rotation speed is adjusted by positional movement of a user. For example, the treadmill 3A may be an automatic treadmill, in which the tilt angle or rotation speed of the track part 4 changes as a user moves to a front region or a rear region of the track part 4.

An exercise item may be an exercise speed of a user in the exercise machine 3. For example, the exercise item may be an exercise speed of a user on the treadmill 3A.

The exercise item may include a plurality of items. For example, the exercise item may further include at least one of a heart rate and a body temperature of a user in addition to the exercise speed of the user.

The input unit 100 receives a user input. The input unit 100 receives a user input via the user's hand movement. The input unit 100 may receive a target exercise speed on the treadmill 3A. The input unit 100 may further receive at least one of a target heart rate and a target body temperature of a user on the treadmill 3A.

For example, the input unit 100 may include a touch pad. The touch pad receives a user input using a contact electrostatic capacitive method, a pressure resistive film method, an infrared detection method, a surface acoustic wave propagation method, an integral strain gauge method, or a piezoeffect method. However, the input unit 100 is not limited to a touch pad but may be implemented using various methods. For example, the input unit 100 may include a keypad, a dome switch, a jog wheel, or a jog switch.

The input unit 100 may be arranged in an electronic device 2. The electronic device 2 may be a portable terminal but is not limited thereto. The electronic device 2 may be modified variously. In an embodiment, the electronic device 2 may be a control panel fixedly installed in the treadmill 3A. In another embodiment, the electronic device 2 may be a display arranged separately from the treadmill 3A.

The detection unit 200 may detect an actual exercise item of a user on the treadmill 3A. The user's actual exercise item may be the user's actual exercise speed. The detection unit 200 may detect a rotation speed of the track part 4 and detect a user's actual exercise speed based on the rotation speed of the track part 4. The detection unit 200 may further include a heart rate detector (not shown) that detects a user's actual heart rate.

The detection unit 200 may be installed in the exercise machine 3. For example, the detection unit 200 may be installed in the treadmill 3A. However, the arrangement of the detection unit 200 is not limited thereto and may be changed according to necessity.

An actual exercise item detected by the detection unit 200 or data related thereto may be transmitted to the exercise guide unit 300. For this, communication units 401 and 402 may be respectively arranged in the exercise machine 3 and the electronic device 2.

The communication units 401 and 402 may include at least one of a mobile communication unit, a short-range wireless communication unit, and a wired communication unit. The mobile communication unit exchanges radio signals with at least one of a base station, an external terminal, and a server in a mobile communication network. The short-range wireless communication unit may include a Bluetooth communication unit, a Bluetooth low energy (BLE) communication unit, a near field communication unit, a wireless local area network (WLAN) (or Wi-Fi) communication unit, a Zigbee communication unit, an infrared data association (IrDA) communication unit, a Wi-Fi direct (WFD) communication unit, an ultra wideband (UWB) communication unit, an ANT+ communication unit, but is not limited thereto. The wired communication unit may exchange data with an external device through a cable or a wired terminal.

The exercise guide unit 300 may provide exercise information for a user so that the user personally controls an exercise speed. For example, the exercise guide unit 300 provides a user with exercise information related to a target exercise speed and an actual exercise speed.

In an embodiment, the exercise guide unit 300 may provide a target exercise speed itself and an actual exercise speed itself for a user.

In another embodiment, the exercise guide unit 300 may inform a user when the difference between a target exercise speed and an actual exercise speed is beyond a certain error range. For example, the exercise guide unit 300 may provide a different message according to a difference between a target exercise speed and an actual exercise speed. When the actual exercise speed is lower than the target exercise speed and the difference therebetween is beyond a certain error range, a first message indicating speed up may be provided. When the actual exercise speed is higher than the target exercise speed and the difference therebetween is beyond the certain error range, a second message indicating speed down may be provided.

Here, the certain error range may be determined using at least one of a particular percentage of the target exercise speed or a particular speed value. In an embodiment, the certain error range may be determined as 10% of the target exercise speed. In another embodiment, the certain error range may be determined as 1 km/h. In a further embodiment, the certain error range may be determined mixedly using the particular percentage of the target exercise speed and the particular speed value together. For example, the certain error range may be determined using the particular speed value when a speed is low and using the particular percentage when the speed is high.

In a further embodiment, the exercise guide unit 300 may score the proximity of an actual exercise speed to a target exercise speed and provide a score to a user. For example, the exercise guide unit 300 may score a difference between the target exercise speed and the actual exercise speed in real time and provide an accumulated score to the user. For example, the exercise guide unit 300 may score the ratio between the target exercise speed and the actual exercise speed in real time and provide an accumulated score to the user. For example, the exercise guide unit 300 may score the ratio between the target exercise speed and the actual exercise speed in real time, accumulate scores, divide an accumulated score by a total time, and provide a division result to the user.

The exercise guide unit 300 may further provide information related to other items besides an exercise speed. For example, the exercise guide unit 300 may further provide information related to a user's actual heart rate and a target heart rate.

The exercise guide unit 300 may visually provide exercise information to a user. For this, the exercise guide unit 300 may include a display.

However, a method by which the exercise guide unit 300 provides exercise information is not limited to those described above, and the exercise guide unit 300 may provide exercise information using auditory or tactile sense.

For this, the exercise guide unit 300 may include at least one of a sound output unit and a vibration generator.

The display unit visually displays information processed in the exercise guide system 1. The display unit may display an object indicating an application execution result.

The display unit may include at least one of a liquid crystal display, a thin film transistor-liquid crystal display, an organic light-emitting diode, a flexible display, a three-dimensional (3D) display, and an electrophoretic display.

The sound output unit outputs audio data, which is received from the communication unit 402 or stored in memory. The sound output unit outputs a sound signal related to a function (e.g., a message reception sound or a notification sound) performed in the exercise guide system 1. The sound output unit may include a speaker, a buzzer, etc.

The vibration generator outputs vibration data, which is received from the communication unit 402 or stored in memory. The vibration generator may include a vibration motor.

A user may personally adjust an exercise speed based on information provided by the exercise guide unit 300.

For example, when the information provided by the exercise guide unit 300 is the first message indicating speed up, the user may increase an actual exercise speed. For example, the user may increase the actual exercise speed by moving to a front sloped region 4-1 of the track part 4.

When the information provided by the exercise guide unit 300 is the second message indicating speed down, the user may decrease the actual exercise speed. For example, the user may decrease the actual exercise speed by moving to a rear sloped region 4-2 of the track part 4.

As such, the exercise guide system 1 provides a user with information about a difference between a target exercise speed and an actual exercise speed, so that the user may exercise at approximately the target exercise speed according to the user's free will.

Differently from the present disclosure, when a track part of a treadmill is configured to be forcedly rotated by a motor at a target exercise speed input by a user, the user is compelled to exercise at the target exercise speed regardless of his/her current body condition. In such treadmill, the rotation of the track part should be stopped when the user does not keep up with the target exercise speed, and the user may be injured when the rotation of the track part is not stopped. In addition, when an actual exercise speed of the user is not constant and has a deviation, the user may feel uneasy on the track part due to the difference between the user's actual exercise speed and the rotation speed of the track part.

Differently from the present disclosure, when a user exercise on a treadmill, of which the speed is controllable according to the user's free will, without the exercise guide system 1, it is difficult for the user to grasp a difference between a target exercise speed and an actual exercise speed, and therefore, the user tends to exercise at random speeds and thus ends up performing an irregular exercise.

However, according to the present disclosure, the exercise guide system 1 guides a user in an exercise on the treadmill 3A of which the speed is controllable according to the user's free will, so that the user may perform an exercise according to his/her current body condition. Since the user may easily grasp a difference between a target exercise speed and an actual exercise speed due to the exercise guide system 1, the user may achieve a certain exercise goal while exercising on his/her own free will.

The embodiments have been described focusing on an example, in which the detection unit 200 of the exercise guide system 1 is arranged in the exercise machine 3 and the input unit 100 and the exercise guide unit 300 of the exercise guide system 1 are arranged in the electronic device 2.

Figure 3A:
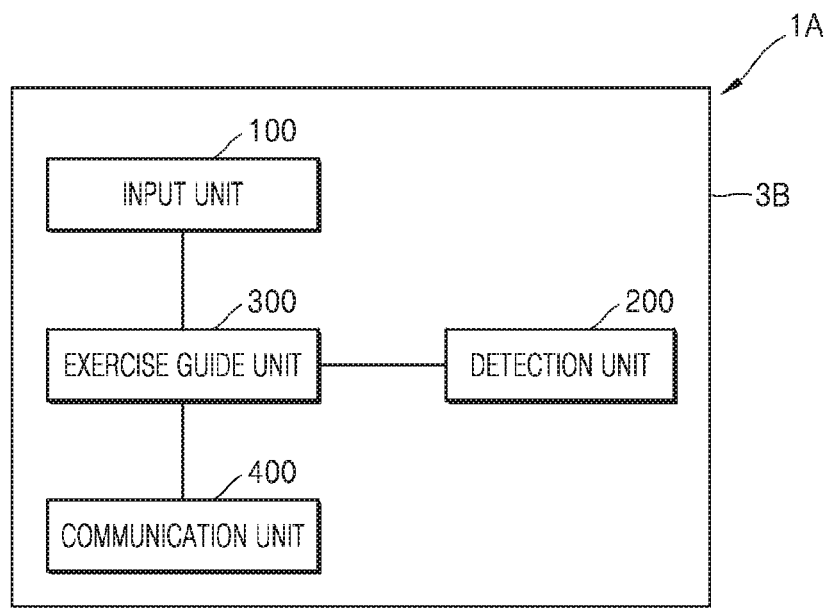
FIGS. 3A, 3B and 3C are diagrams of the configurations of exercise guide systems according to different embodiments.
Figure 3B:
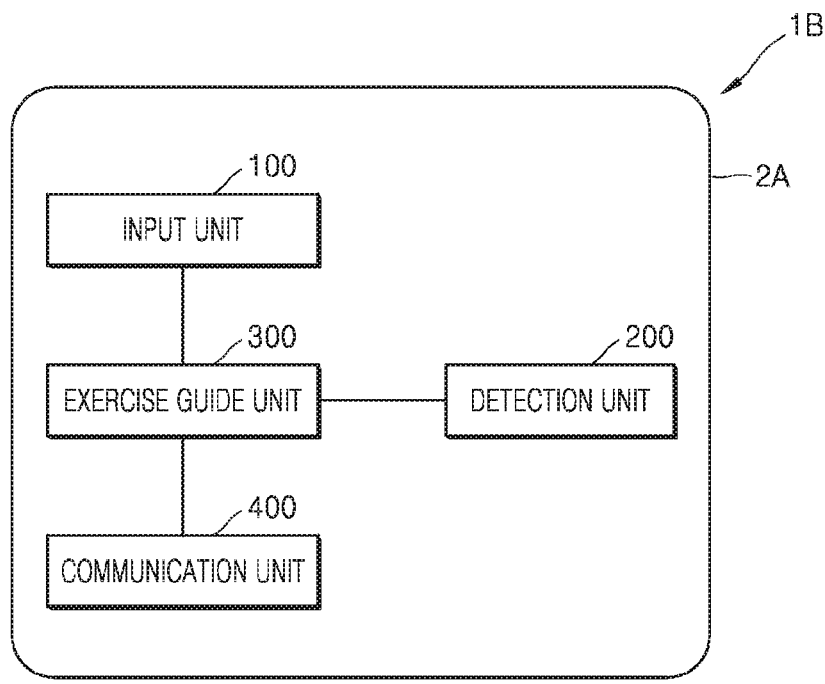
Figure 3C:
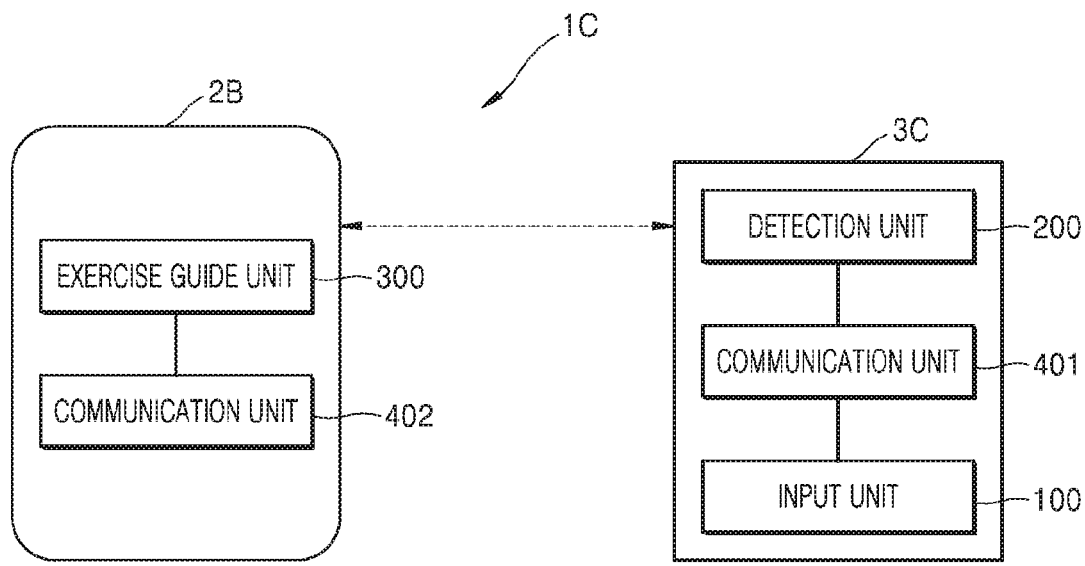

However, the arrangement of each element of the exercise guide system 1 is not limited thereto and may be various. In an embodiment, all elements of the exercise guide system 1 may be arranged in a single device. For example, the input unit 100, the detection unit 200, the exercise guide unit 300, and a communication unit 400 of an exercise guide system 1A or 1B may all be arranged in an exercise machine 3B as shown in FIG. 3A or in an electronic device 2A as shown in FIG. 3B. In another embodiment, as shown in FIG. 3C, the input unit 100 and the detection unit 200 of an exercise guide system 1C may be arranged in an exercise machine 3C and the exercise guide unit 300 of the exercise guide system 1C may be separately arranged in an electronic device 2B.

Figure 4:
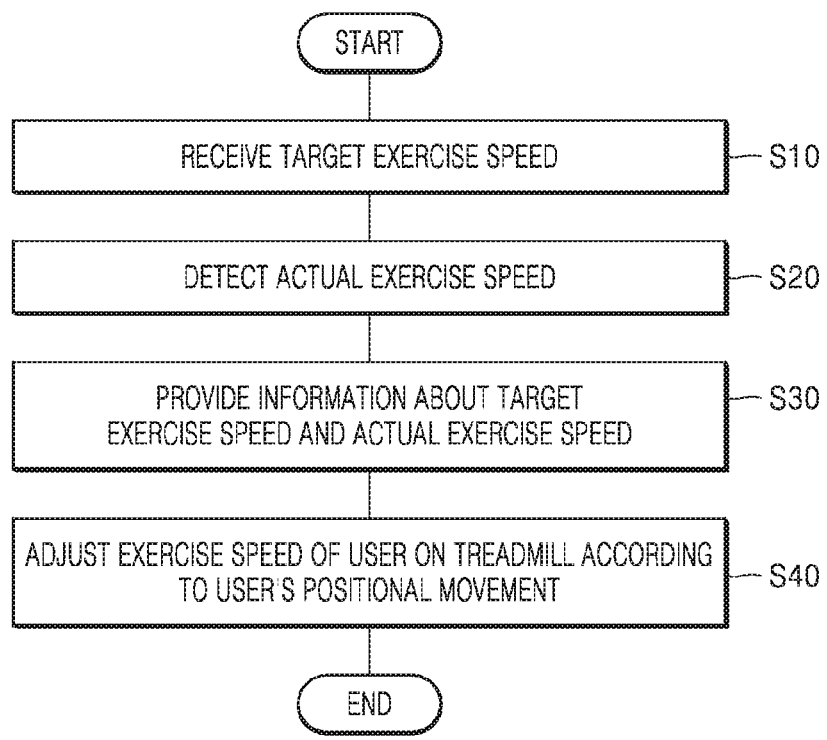
FIG. 4 is a flowchart of an exercise method using an exercise guide system, according to an embodiment of the present disclosure.

FIG. 4 is a flowchart of an exercise method using the exercise guide system 1, according to an embodiment of the present disclosure.

The exercise guide system 1 receives a target exercise speed from a user through the input unit 100 in operation S10. The input unit 100 may receive a plurality of target exercise speeds. The plurality of target exercise speeds may be different by time zones. The input unit 100 may enable a target exercise speed to be directly input but is not limited thereto. The input unit 100 may allow an indirect input by enabling an exercise program, in which a target exercise speed has been set, to be selected.

The exercise guide system 1 may detect an actual exercise speed of the user on the treadmill 3A through the detection unit 200 in operation S20.

The exercise guide system 1 provides information about the target exercise speed and the actual exercise speed through the exercise guide unit 300 in operation S30. For example, information about a difference between the target exercise speed and the actual exercise speed may be provided through the exercise guide unit 300.

For example, when the actual exercise speed is beyond a certain error range with respect to the target exercise speed, the exercise guide unit 300 may visually provide a speed change message requesting a change in speed. The speed change message may include a first message indicating speed up and a second message indicating speed down. A method of delivering information provided by the exercise guide unit 300 is not limited to a visual method, but an auditory method or a tactile method may be used.

The user may change his/her position on the treadmill 3A based on the information provided through the exercise guide unit 300. For example, the user moves to the front sloped region 4-1 of the track part 4 to speed up and moves to the rear sloped region 4-2 of the track part 4 to slow down.

An exercise speed of the user on the treadmill 3A may be adjusted according to the user's positional movement in operation S40. In other words, the user is not forced to exercise by a motor but may exercise on his/her own free will while following the target exercise speed.

Figure 5A:
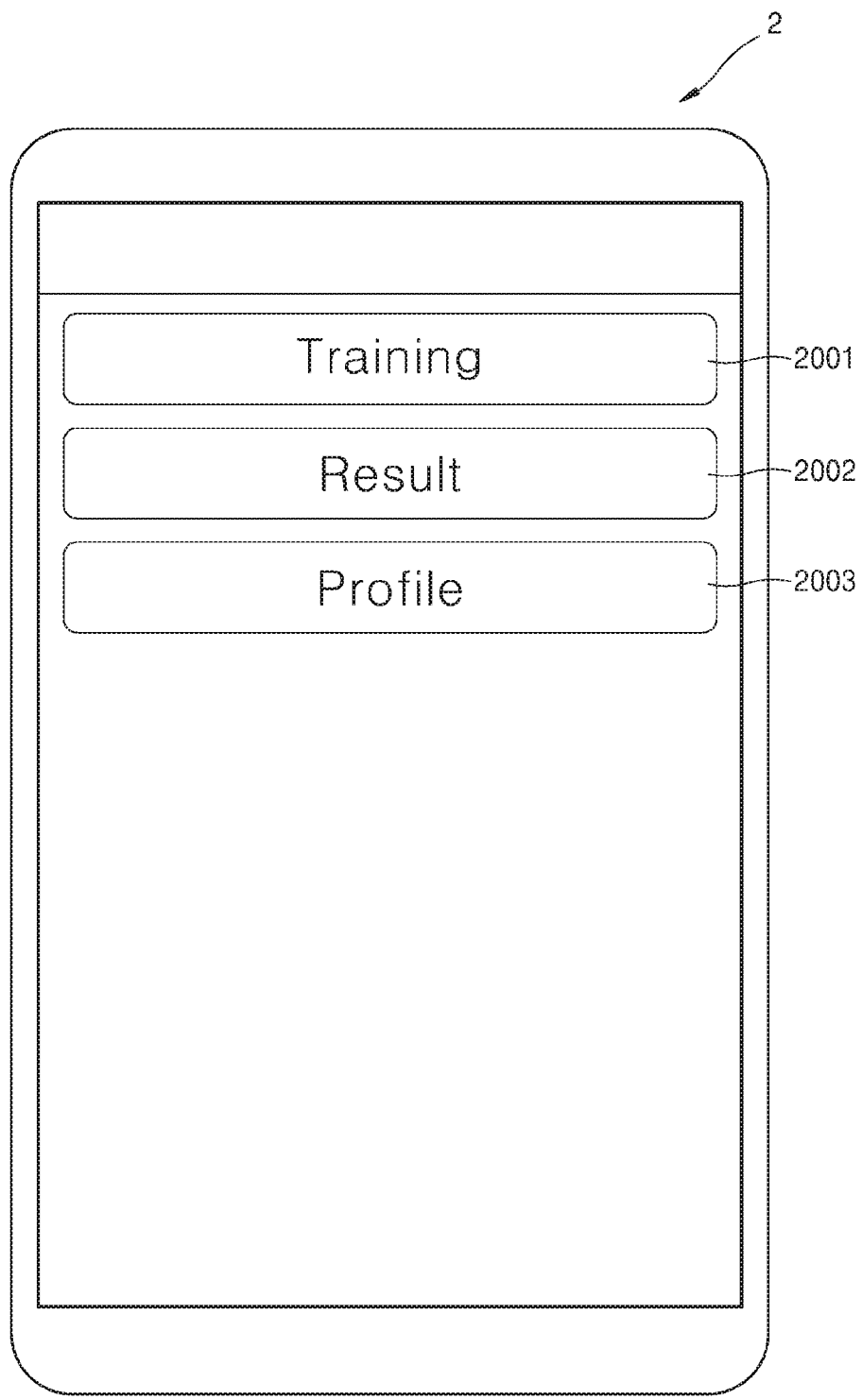
FIGS. 5A, 5B and 5C show screens enabling a user to input a target exercise speed in an exercise guide system, according to an embodiment.
Figure 5B:
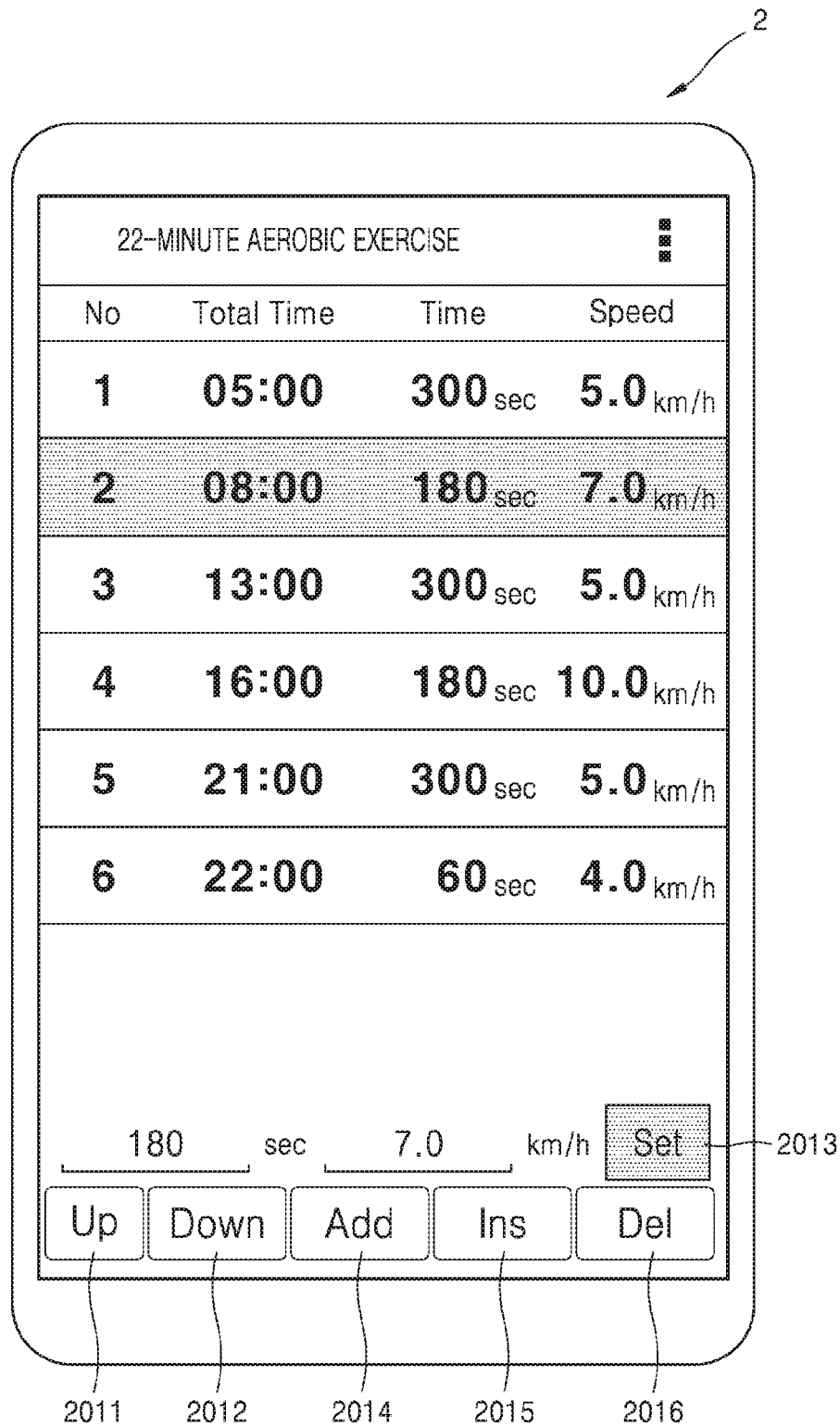
Figure 5C:
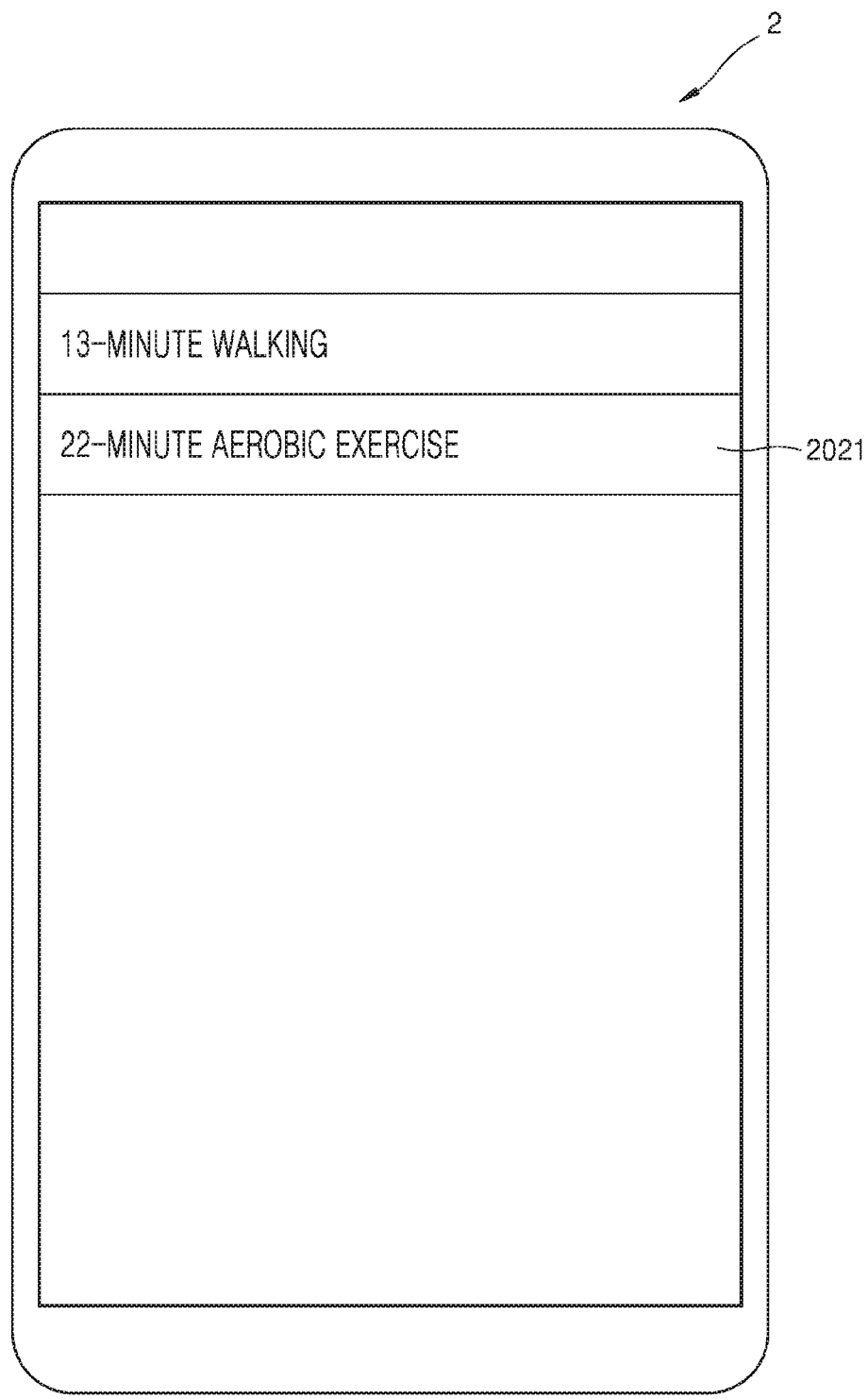

FIGS. 5A, 5B and 5C show screens enabling a user to input a target exercise speed in the exercise guide system 1, according to an embodiment.

Referring to FIG. 5A, a plurality of icons are activated on an initial screen. For example, a "Training" icon 2001, a "Result" icon 2002, and a "Profile" icon 2003 are activated on the initial screen.

The "Training" icon 2001 is selected to start an exercise. The "Result" icon 2002 is selected to check the exercise result after finishing the exercise. The "Profile" icon 2003 is selected to directly design a target exercise before starting the exercise.

Referring to FIG. 5B, when the "Profile" icon 2003 is selected, a screen for inputting a target exercise speed is displayed in the exercise guide system 1. Icons, e.g., an "Up" icon 2011, a "Down" icon 2012, and a "Set" icon 2013, for inputting a target exercise time and a target exercise speed are displayed on the screen.

In addition, icons, e.g., an "Add" icon 2014, an "Ins" icon 2015, and a "Del" icon 2016, for inputting and deleting a plurality of target exercise speeds and target exercise times are displayed on the screen. A new target exercise time and a new target exercise speed may be added to the end of a list by selecting the "Add" icon 2014. A new target exercise time and a new target exercise speed may be inserted into a certain position in the list by selecting the "Ins" icon 2015 at the certain position. A portion of the list may be deleted by selecting the "Del" icon 2016.

As such, an exercise program having various target exercise speeds by time zones may be designed. For example, an aerobic program having a plurality of target exercise speeds for about 22 minutes may be designed.

Referring back to FIG. 5A, the user may return to the initial screen after designing a target exercise program. When the user wants to start an exercise, the user selects the "Training" icon 2001 on the initial screen.

Referring to FIG. 5C, an exercise program, which has been designed by the user, is displayed in the exercise guide system 1. For example, an exercise program 2021 for a 22-minute aerobic exercise shown in FIG. 5B is displayed. The user may select a desired exercise program and input a target exercise speed during a target exercise time. However, the inputting of a target exercise speed is not limited thereto and may be performed in various manners.

Figure 6:
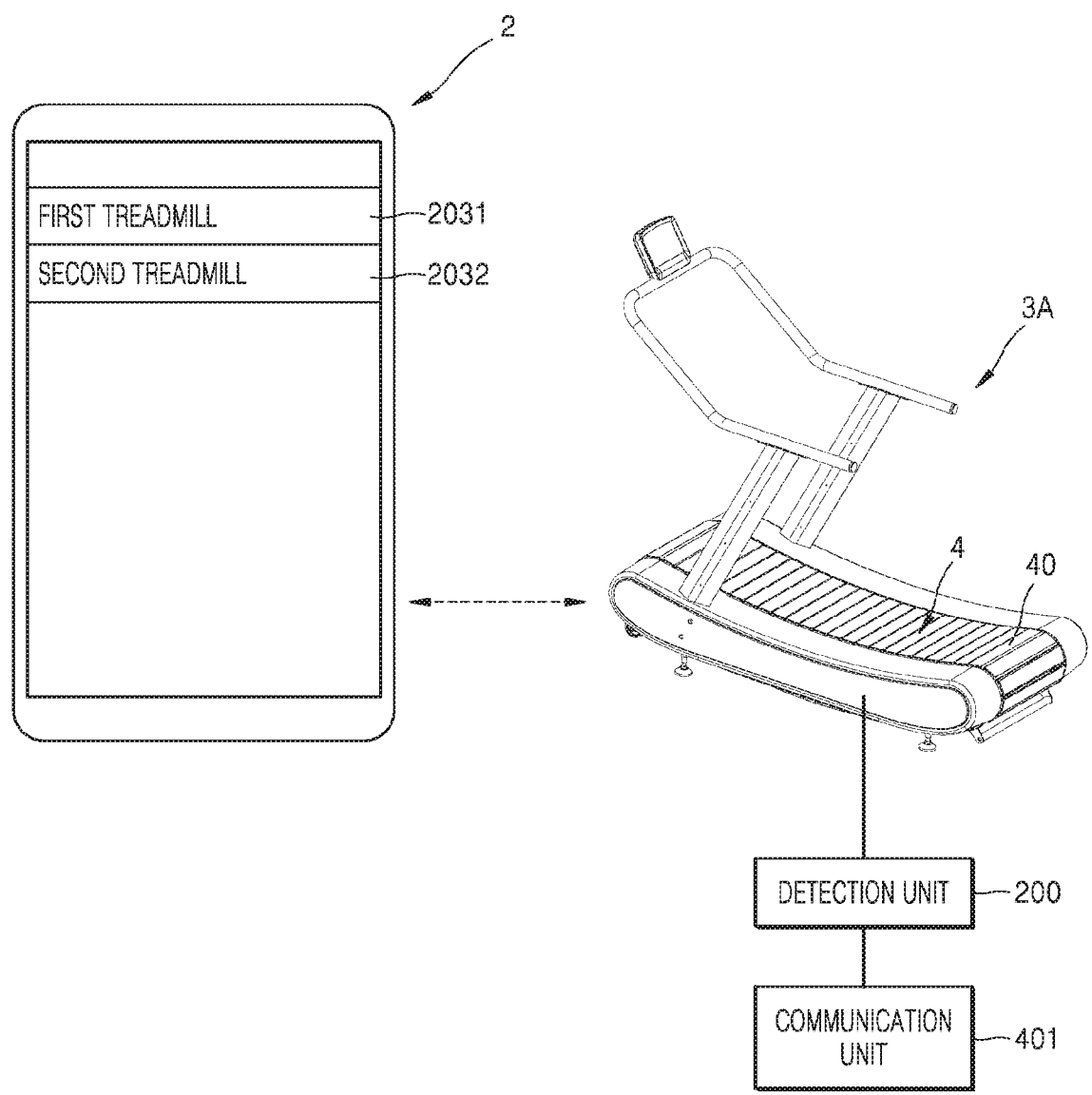
FIG. 6 is a diagram for explaining a procedure for detecting an actual exercise speed and transmitting data corresponding to a detection result in an exercise guide system, according to an embodiment.

FIG. 6 is a diagram for explaining a procedure for detecting an actual exercise speed and transmitting data corresponding to a detection result in the exercise guide system 1, according to an embodiment.

Referring to FIG. 6, the detection unit 200 detects a rotation speed of the track part 4 of the treadmill 3A in real time. Detected data is transmitted to outside the treadmill 3A through the communication unit 401 of the treadmill 3A. The treadmill 3A currently discovered by searching is displayed as an icon on the electronic device 2. For example, the electronic device 2 displays icons 2031 and 2032 respectively for a first treadmill and a second treadmill, which have been currently discovered by searching.

The user selects an icon for a treadmill, on which the user is positioned, e.g., the icon 2031 for the first treadmill. Accordingly, the electronic device 2 may be connected to the treadmill 3A on which the user is positioned, and data may be transmitted from the treadmill 3A to the electronic device 2 and displayed on the electronic device 2.

The screen of the electronic device 2 shown in FIG. 6 may be displayed before the screen for selecting an exercise program in FIG. 5C, but the present disclosure is not limited thereto. The screen of the electronic device 2 shown in FIG. 6 may be displayed after the screen for selecting an exercise program in FIG. 5C.

Figure 7A:
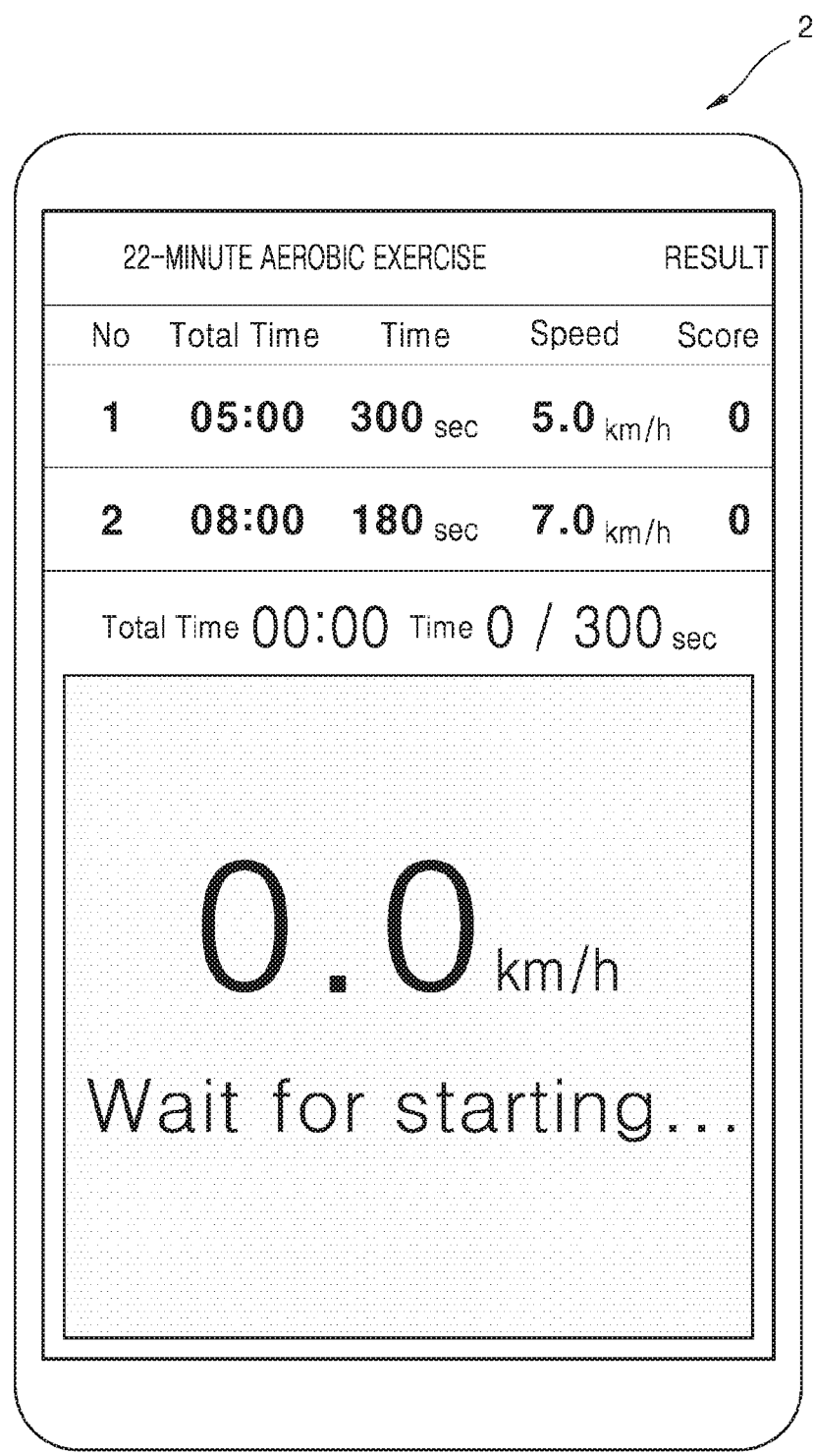
FIGS. 7A, 7B and 7C show exercise standby screens of an exercise guide system before an exercise is started, according to an embodiment.
Figure 7B:
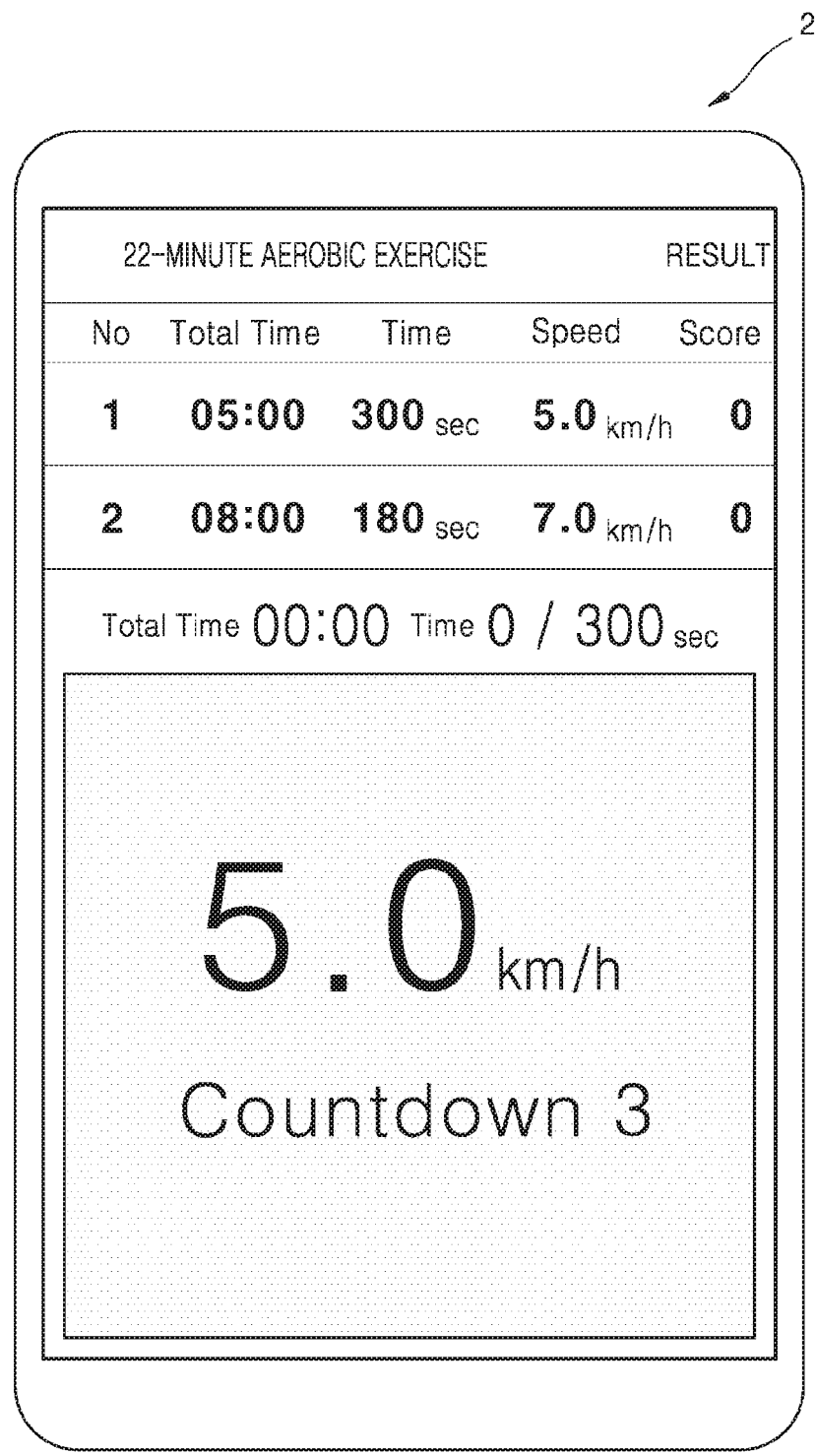
Figure 7C:
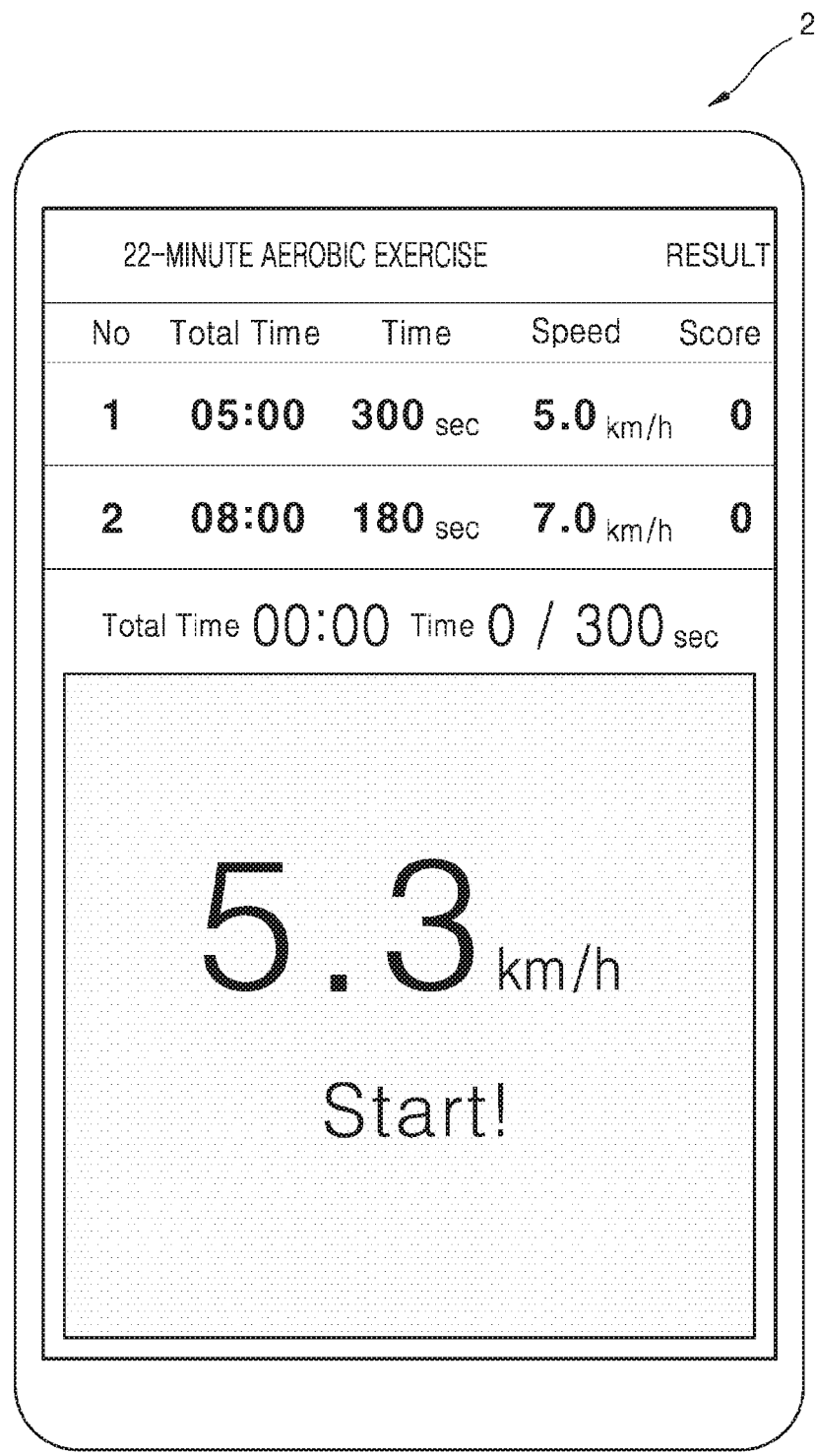

FIGS. 7A, 7B and 7C show exercise standby screens of the exercise guide system 1 before an exercise is started, according to an embodiment. Referring to FIG. 7A, when an actual exercise speed is 0.0 km/h or is lower than a certain reference speed, e.g., 0.2 km/h, the exercise guide system 1 may display a message indicating that it waits for start of an exercise, e.g., a "Wait for starting" message. Referring to FIGS. 7B and 7C, the exercise guide system 1 may display a mark indicating start when an actual exercise speed is equal to or higher than the certain reference speed so that a user may be ready to start an exercise.

Figure 8A:
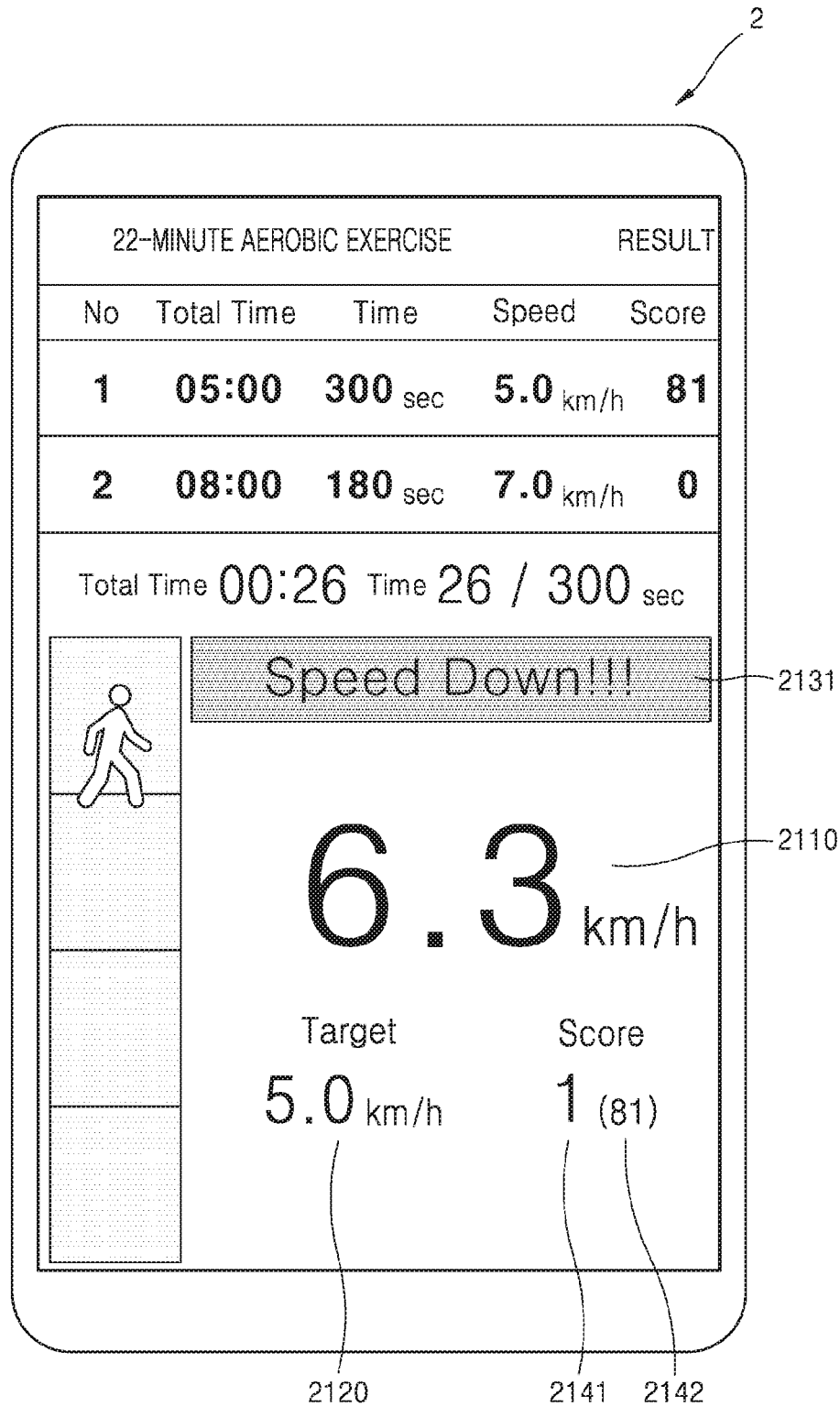
FIGS. 8A, 8B and 8C show screens for providing a user with information related to a target exercise speed and an actual exercise speed in an exercise guide system, according to an embodiment.
Figure 8B:
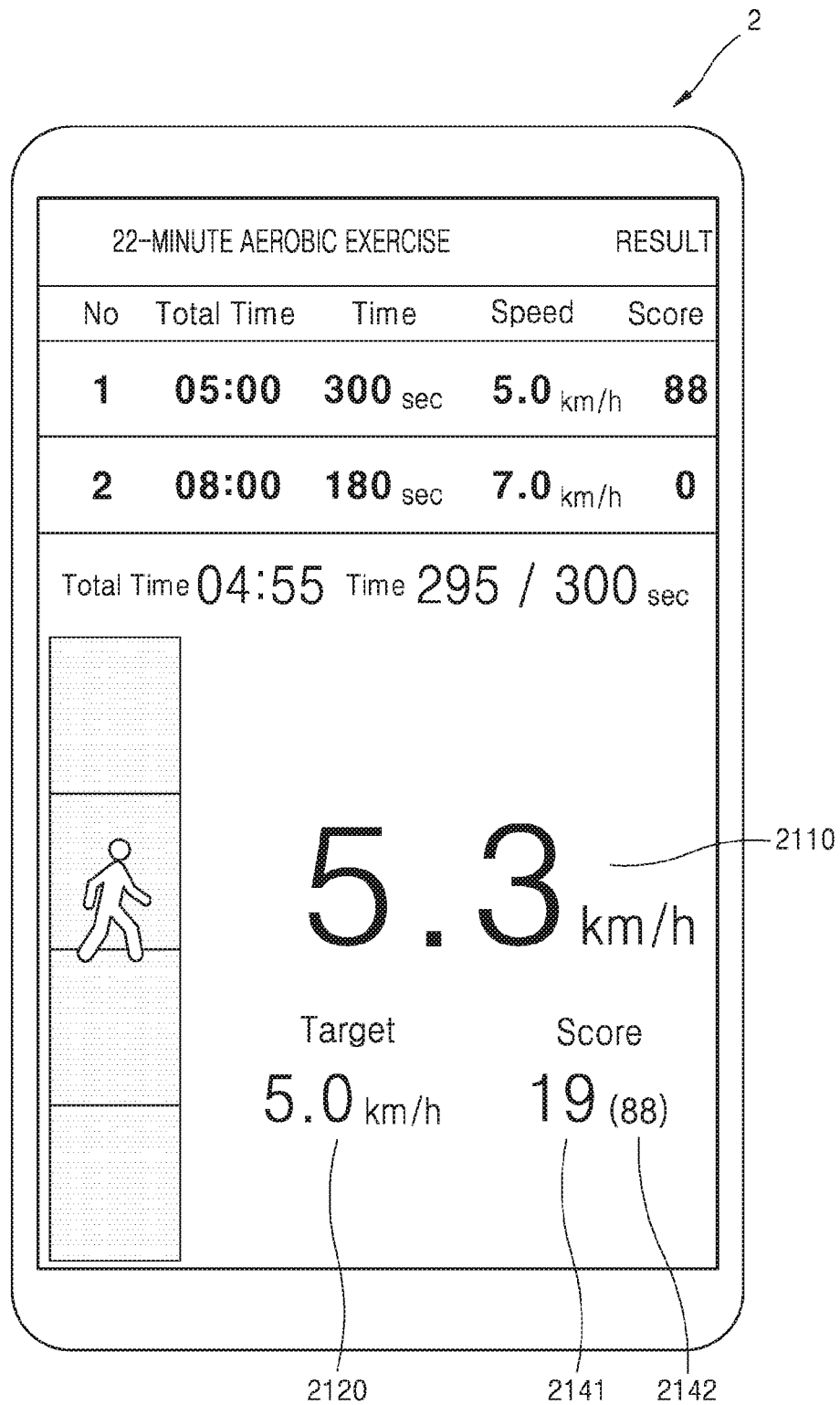
Figure 8C:
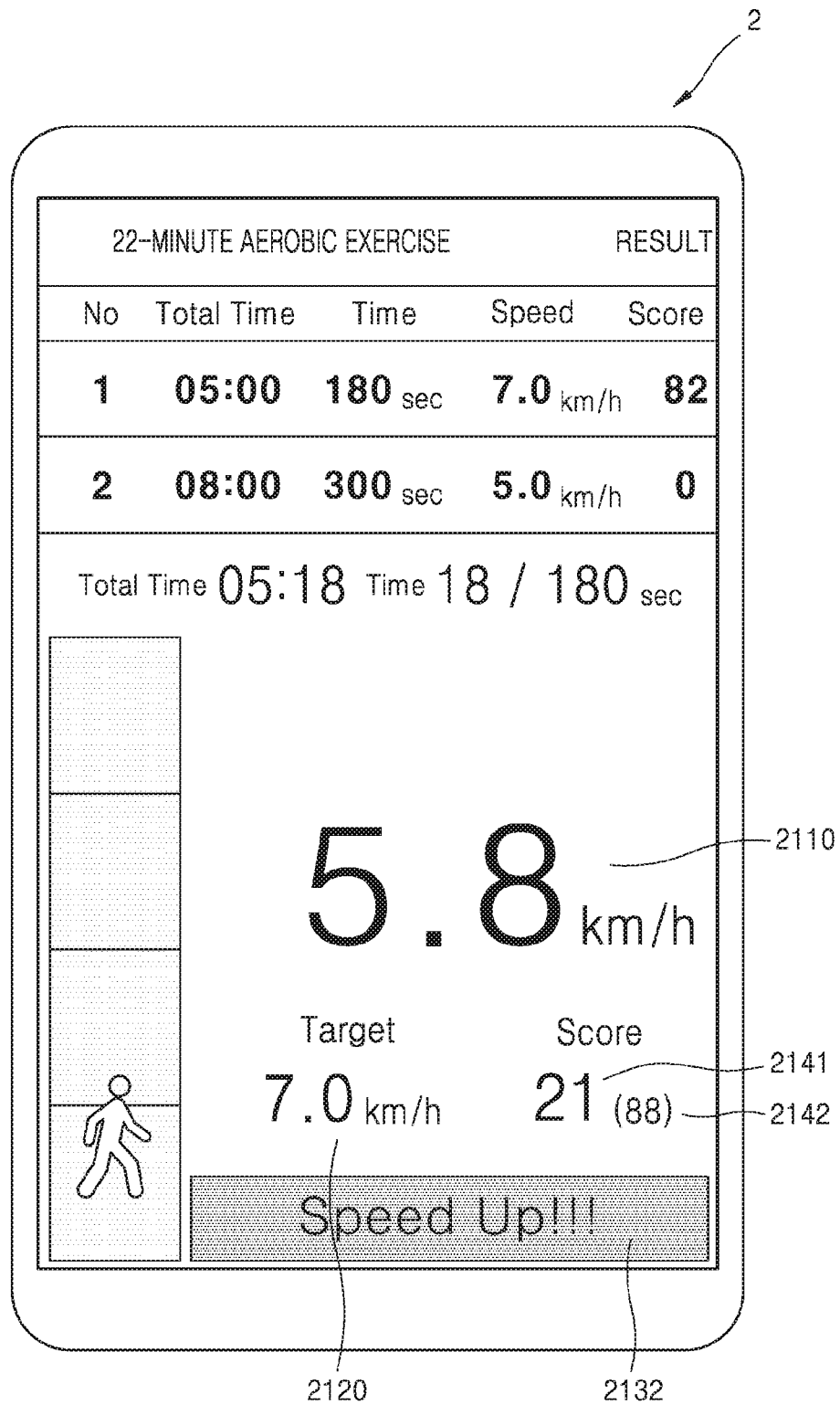

FIGS. 8A, 8B and 8C show screens for providing a user with information related to a target exercise speed and an actual exercise speed in the exercise guide system 1, according to an embodiment.

Referring to FIG. 8A, the electronic device 2 displays an actual exercise speed 2110 of the user and a target exercise speed 2120. For example, the electronic device 2 displays an actual exercise speed of 6.3 km/h and a target exercise speed of 5.0 km.

When the actual exercise speed 2110 is higher than the target exercise speed 2120 and is beyond an error range, the electronic device 2 may display an additional item to the user besides the actual exercise speed 2110 and the target exercise speed 2120. For example, the electronic device 2 may display a first message 2131 indicating speed down.

Referring to FIG. 8B, when a difference between the actual exercise speed 2110 and the target exercise speed 2120 is within the error range, the electronic device 2 may display only the actual exercise speed 2110 and the target exercise speed 2120 but not a message indicating to change speed.

Referring to FIG. 8C, when the actual exercise speed 2110 is lower than the target exercise speed 2120 and is beyond the error range, the electronic device 2 may display an additional item to the user besides the actual exercise speed 2110 and the target exercise speed 2120. For example, the electronic device 2 may display a second message 2132 indicating speed up.

Referring to FIGS. 8A through 8C, a user's actual exercise may be scored with respect to a target exercise, and a score may be displayed on a screen. For example, a case in which the user performs the actual exercise within an error range of a target exercise speed during a total target exercise time may be scored 100, and a ratio of the actual exercise performed till a current exercise time to the target exercise may be displayed as a first score 2141. In addition, a case in which the user performs the actual exercise within the error range of the target exercise speed till the current exercise time may be scored 100, and a ratio of the actual exercise performed till the current exercise time to the target exercise may be displayed as a second score 2142.

The user may personally change the actual exercise speed 2110 based on information provided to the electronic device 2. Accordingly, the user may perform an exercise within the error range of the target exercise speed 2120. In addition, since a current exercise state and a final exercise state are respectively provided as the first and second scores 2141 and 2142, the user may be motivated to achieve an exercise goal.

Figure 9A:
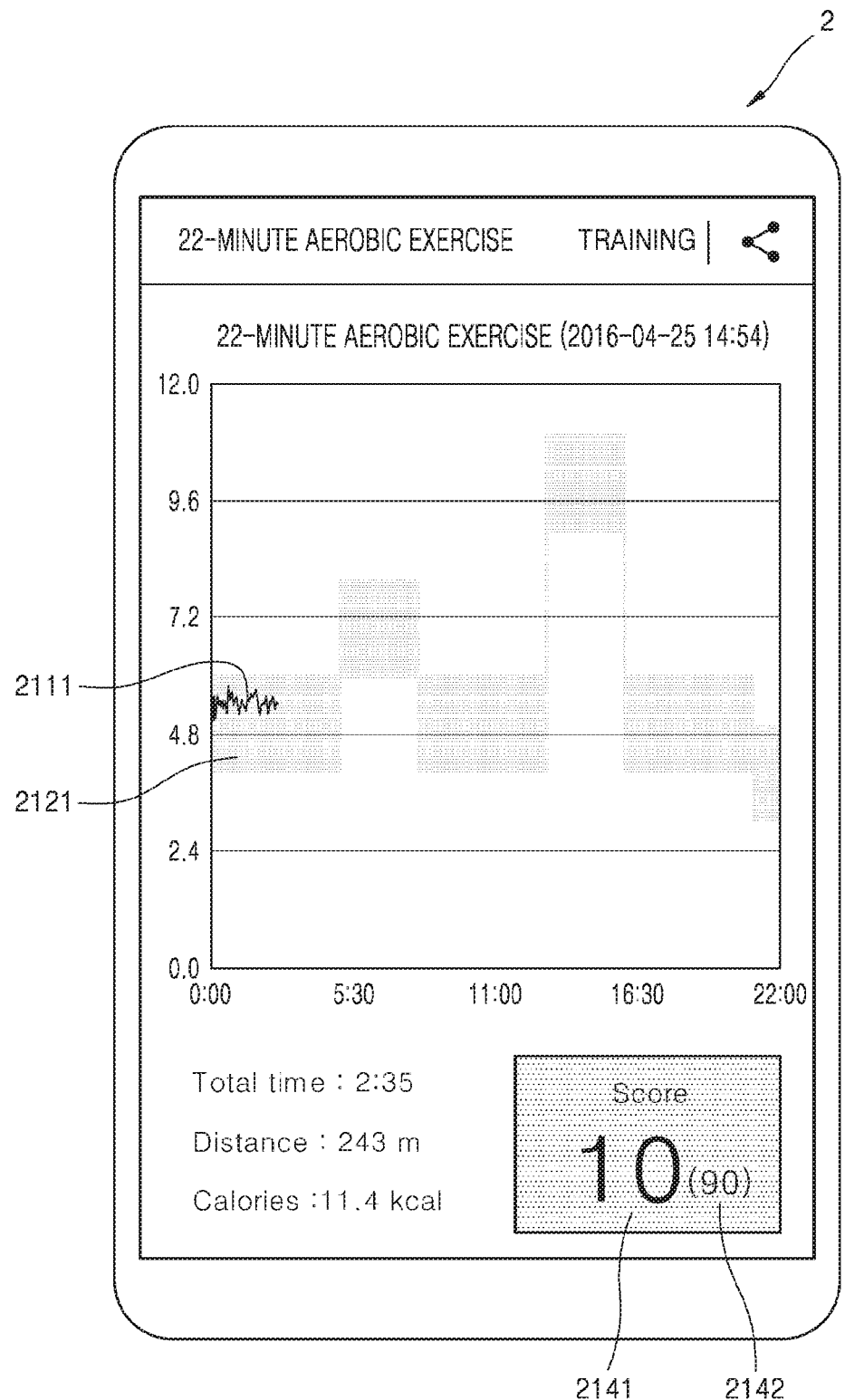
FIGS. 9A, 9B and 9C show screens for providing a user with information related to a target exercise speed and an actual exercise speed as graphs in an exercise guide system, according to an embodiment.
Figure 9B:
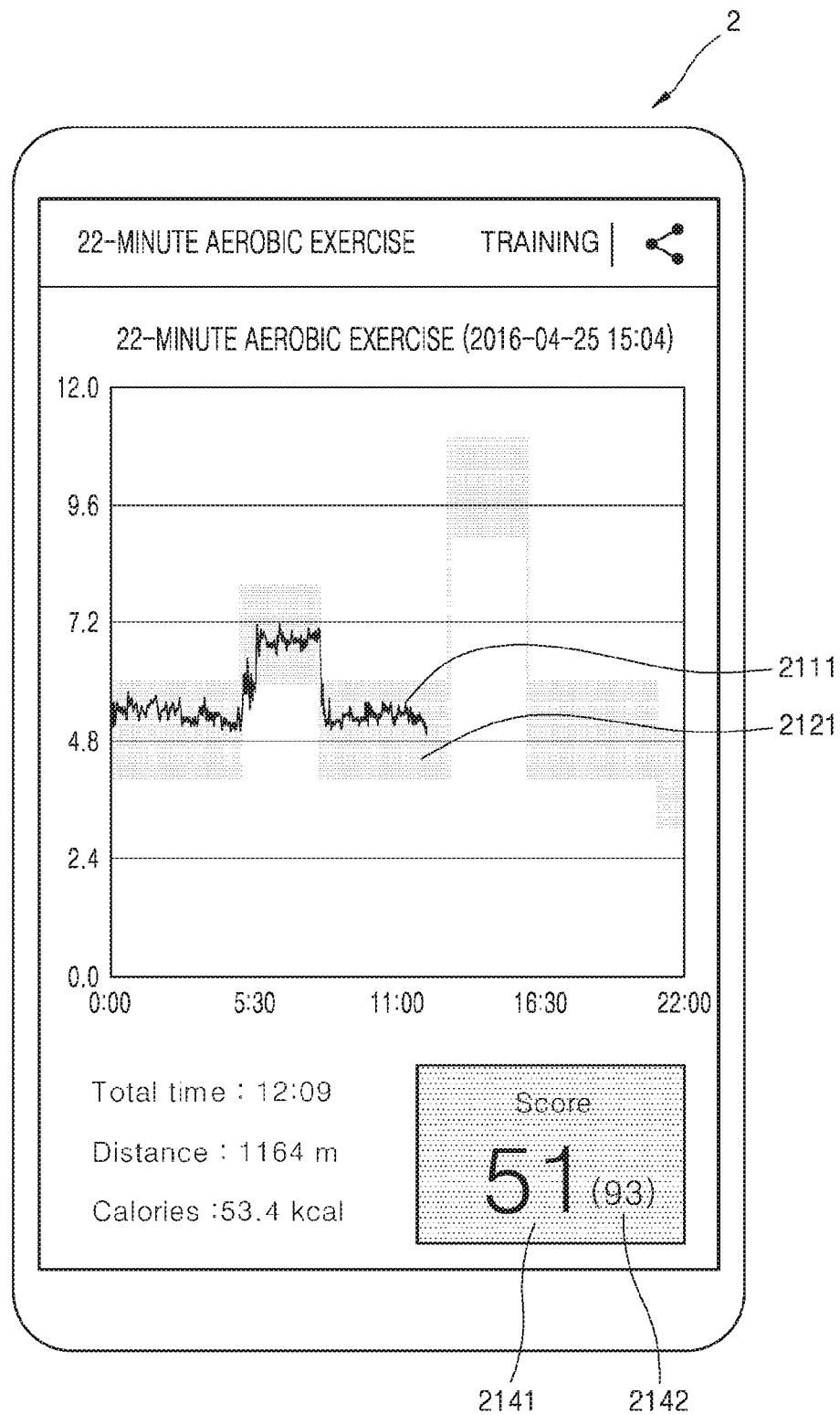
Figure 9C:
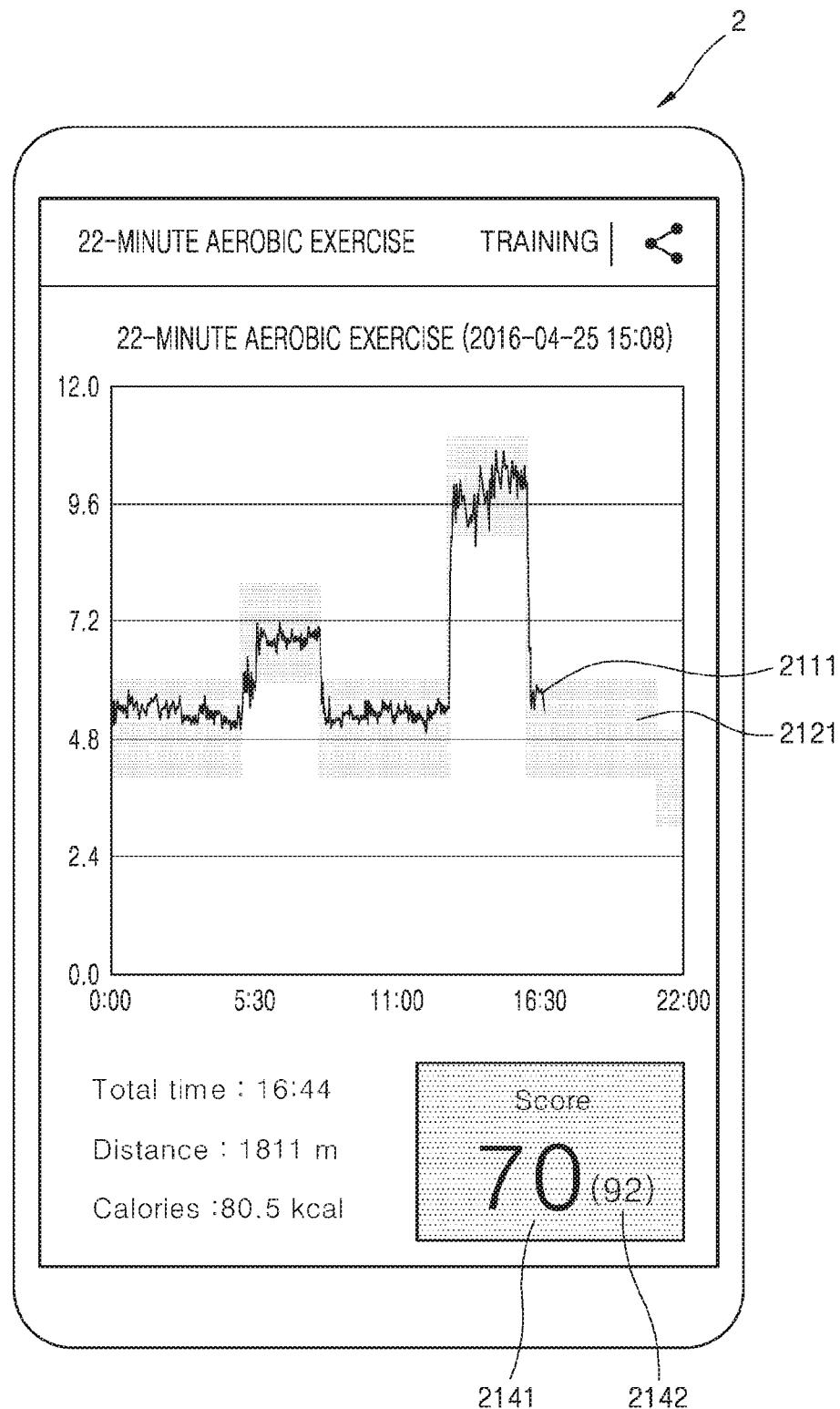

FIGS. 9A, 9B and 9C show screens for providing a user with information related to the target exercise speed 2120 and the actual exercise speed 2110 in graphs in the exercise guide system 1, according to an embodiment Referring to FIGS. 9A through 9C, an error range 2121 of a target exercise speed and an actual exercise speed 2111 are displayed in graphs. At this time, an exercise score for total exercise duration and an exercise score up to now may be displayed on the electronic device 2.

The actual exercise speed 2111 of the user is not regular but variable. This is because the user exercises on a manual treadmill rotated by the user, not a treadmill rotated by a motor at a regular speed.

When the exercise guide system 1 provides information about the actual exercise speed 2110 or 2111 and the target exercise speed 2120 for a user exercising on a manual treadmill, the user may perform an exercise on his/her own free will so that the actual exercise speed 2110 follows the target exercise speed 2120 within a certain error range.

Figure 10A:
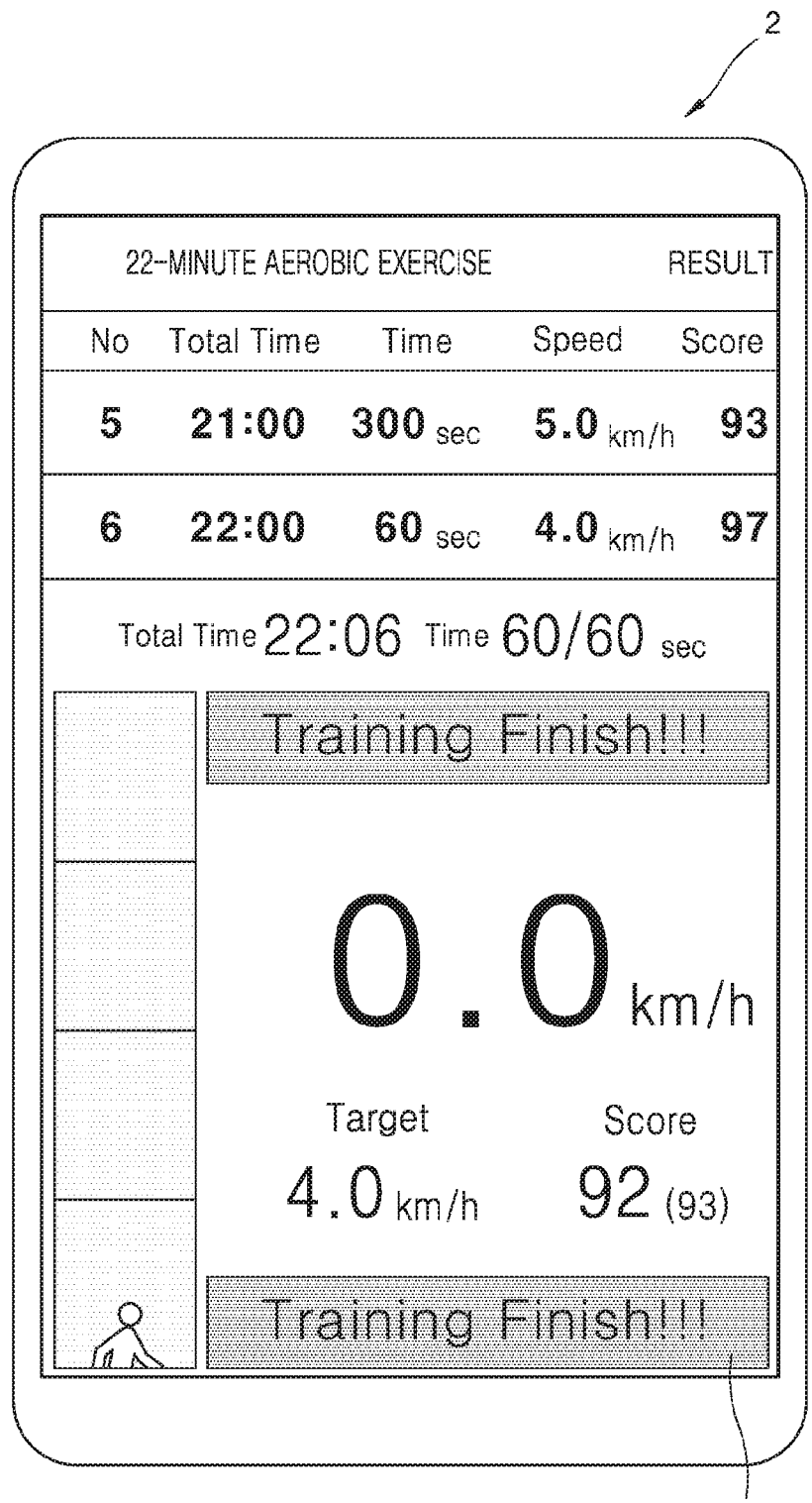
FIGS. 10A and 10B show screens of a state in which a user has finished an exercise.
Figure 10B:
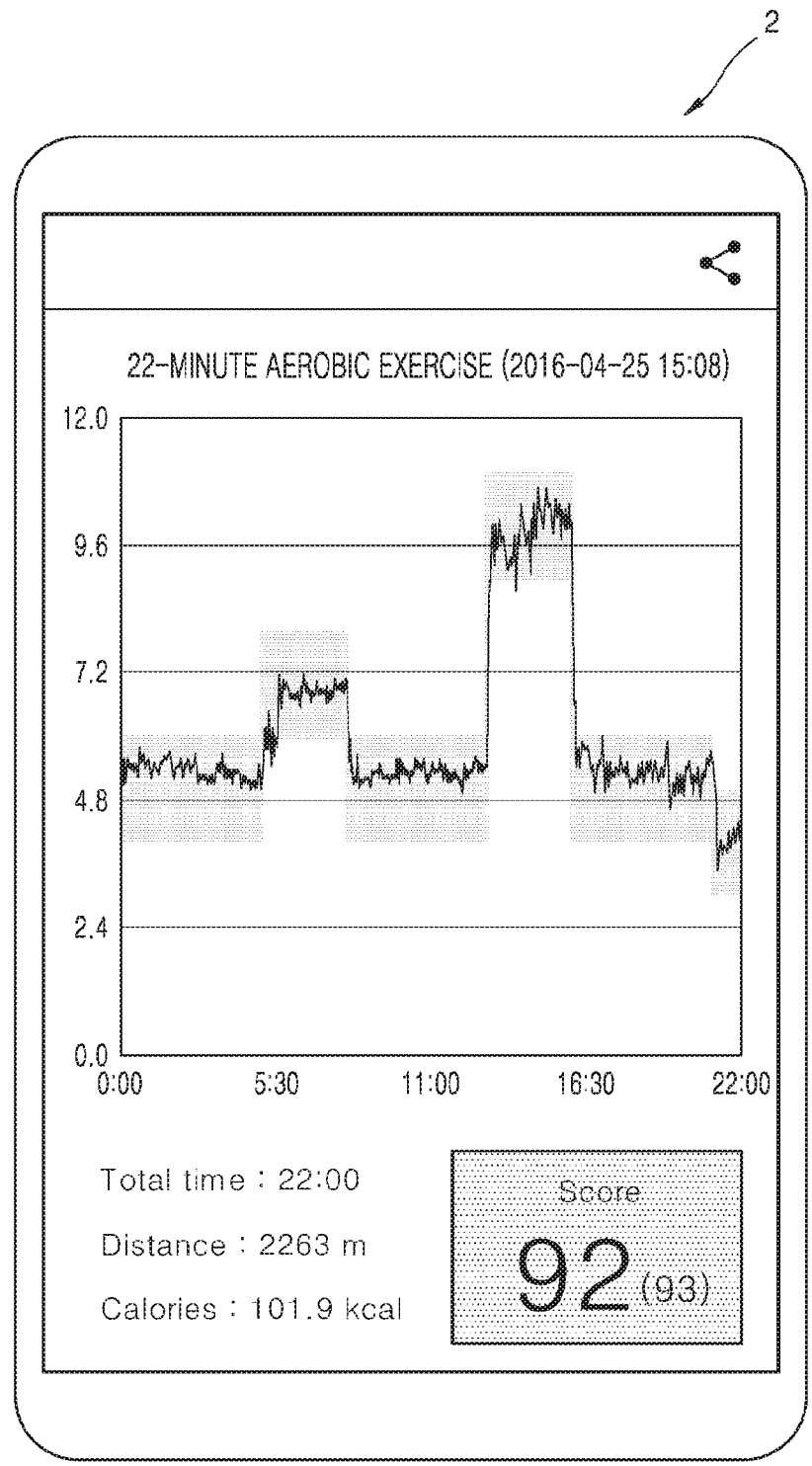

FIGS. 10A and 10B show screens of a state in which a user has finished an exercise. Referring to FIG. 10A, when the user's exercise is finished, an exercise finish message 2133 is displayed. Referring to FIG. 10B, the user's exercise result in each time zone is displayed in a graph.

Figure 11:
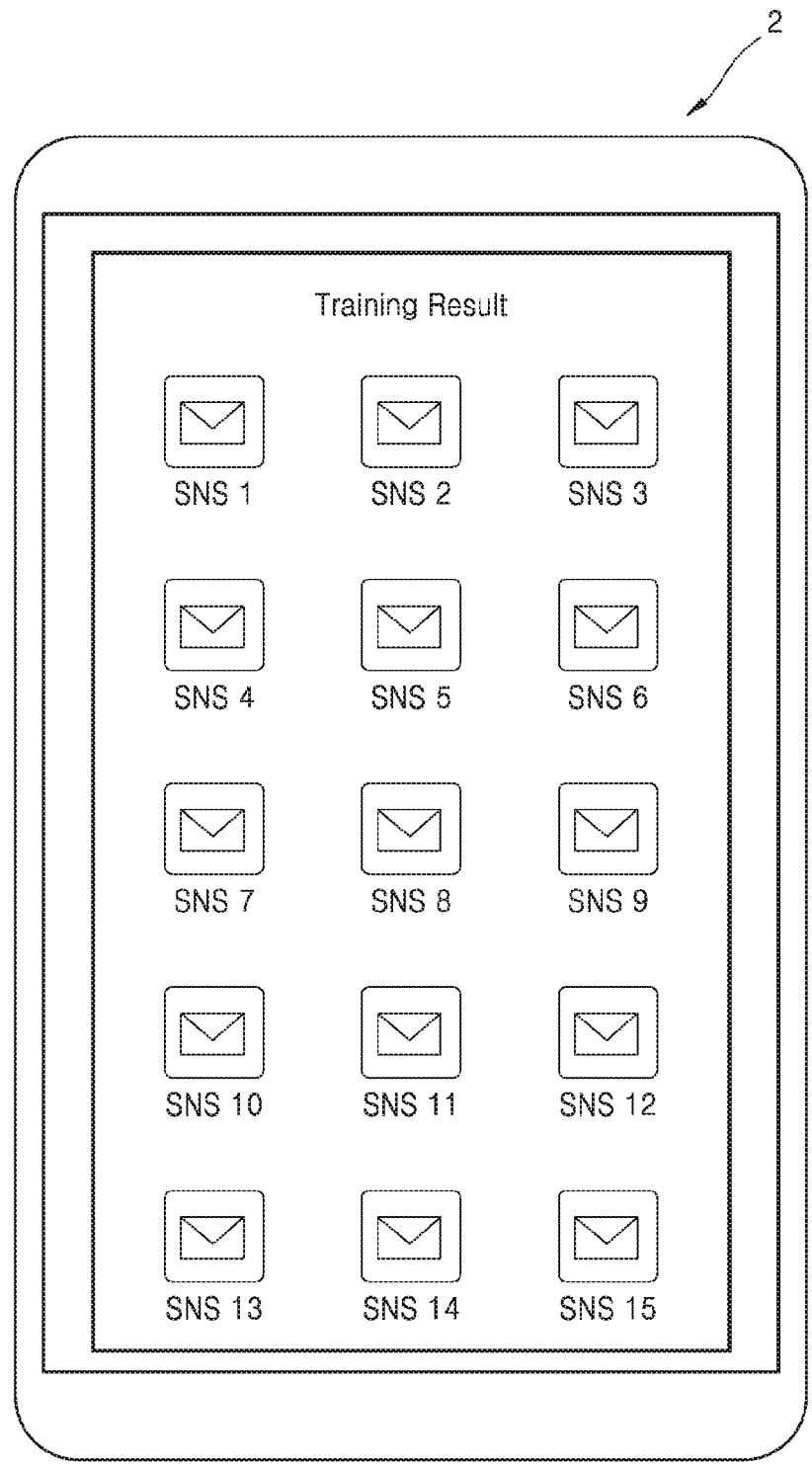
FIG. 11 shows a screen for transmitting an exercise result from an electronic device to outside the electronic device, according to an embodiment.

FIG. 11 shows a screen for transmitting an exercise result from the electronic device 2 to outside the electronic device 2, according to an embodiment. Referring to FIG. 11, the exercise guide system 1 may transmit a user's exercise result to an external device. For example, the exercise guide system 1 may share an exercise result through various types of social networking service (SNS). Accordingly, the exercise guide system 1 enables exercise management without a separate data server or without facing other people, e.g., trainers.

Logical blocks, modules or units described in connection with embodiments disclosed herein can be implemented or performed by a computing device having at least one processor, at least one memory and at least one communication interface. The elements of a method, process, or algorithm described in connection with embodiments disclosed herein can be embodied directly in hardware, in a software module executed by at least one processor, or in a combination of the two. Computer-executable instructions for implementing a method, process, or algorithm described in connection with embodiments disclosed herein can be stored in a non-transitory computer readable storage medium. Although the preferred embodiments of the present disclosure have been described as examples, the scope of the present disclosure is not limited to the preferred embodiments and can be appropriately modified without departing from the scope defined by the claims.

Other aspects, features, and advantages than those described above will be clear from the accompanying drawings, the claims, and the description of embodiments below. These general and specific aspects may be embodied using a system, a method, a computer program, or a combination thereof.

What is claimed is:

1. A manually operated treadmill, comprising:
   a curved track part comprising a plurality of slats configured to be rotated by a user's leg motion without the use of a driving motor, the track part comprising a front sloped region and a rear sloped region;
   an input unit configured to receive an input from the user to set at least one target exercise speed;
   a detection unit configured to detect a rotating speed of the plurality of slats, the rotating speed is variable according to the user's leg movement; and
   an exercise guide unit configured to provide guidance to the user to move to the front sloped region of the curved track part to increase the rotating speed of the plurality of slats in response to the rotating speed of the plurality of slats being less than the target exercise speed, and to move to the rear sloped region of the curved track part to decrease the rotating speed of the plurality of slats in response to the rotating speed of the plurality of slats being greater than the target exercise speed.

2. The manually operated treadmill of claim 1, wherein the exercise guide unit is configured to provide information related to a difference between an actual exercise speed and the target exercise speed.

3. The manually operated treadmill of claim 2, wherein the exercise guide unit is configured to provide the user with the information related to the difference between the actual exercise speed and the target exercise speed when the difference between the actual exercise speed and the target exercise speed is beyond a certain error range.

4. The manually operated treadmill of claim 2, wherein the exercise guide unit is configured to score the difference between the actual exercise speed and the target exercise speed and to provide a score for the user.

5. The manually operated treadmill of claim 2, wherein the exercise guide unit is configured to provide the information using at least one of visual sense, auditory sense, and tactile sense.

6. The manually operated treadmill of claim 1, further comprising a communication unit configured to transmit information provided by the exercise guide unit to outside the manually operated treadmill.

7. The manually operated treadmill of claim 1, wherein the input unit is configured to receive a target heart rate of the user, the detection unit is configured to detect an actual heart rate of the user, and the exercise guide unit is configured to provide information related to the actual heart rate and the target heart rate.

8. An exercise guide system for guiding a user in an exercise on a manual treadmill of which the speed is controllable by the user s leg motion without the use of a driving motor, the exercise guide system comprising:
an input unit configured receive an input from the user to set a plurality of target exercise speeds to be respectively applied to a plurality of time periods, the plurality of time periods comprising first, second and third time periods (t1, t2, t3), the plurality of target exercise speeds being different for each of the plurality of time periods, the plurality of target exercise speeds comprising a first target exercise speed (V1) applied to the first time period (t1), a second target exercise speed (V2) applied to the second time period (t2) and greater than the first target exercise speed (V1) and a third target exercise speed (V3) applied to the third time period (t3) and less than the second target exercise speed (V2);
a detection unit configured to detect a rotation speed of a curved track part of the manual treadmill in order to detect an actual exercise speed of the user on the treadmill; and
an exercise guide unit configured to provide information related to the actual exercise speed and the target exercise speed so that the user adjusts an exercise speed on the manual treadmill, the exercise guide unit further configured to visually provide information whether the actual target exercise speed follows the second target exercise speed (V2) within a predetermined error range, in response to the first target exercise speed (V1) being changed to the second target exercise speed (V2),
wherein the curved track part includes a front sloped region and a rear sloped region.

9. An exercise management method using an exercise guide system for guiding a user in an exercise on a manual treadmill of which the speed is controllable by the user's leg motion without the use of a driving motor, the exercise management method comprising:
receiving an input from the user to set a plurality of target exercise speeds to be respectively applied to a plurality of time periods, the plurality of time periods comprising first, second and third time periods (t1, t2, t3), the plurality of target exercise speeds being different for each of the plurality of time periods, the plurality of target exercise speeds comprising a first target exercise speed (V1) applied to the first time period (t1), a second target exercise speed (V2) applied to the second time period (t2) and greater than the first target exercise speed (V1) and a third target exercise speed (V3) applied to the third time period (t3) and less than the second target exercise speed (V2);
detecting a rotation speed of a curved track part of the manual treadmill in order to detect an actual exercise speed of the user on the treadmill;
providing the user with information related to the actual exercise speed and the target exercise speed so that the user adjusts an exercise speed on the manual treadmill, and
visually providing information whether the actual target exercise speed follows the second target exercise speed (V2) within a predetermined error range, in response to the first target exercise speed (V1) changed to the second target exercise speed (V2),
wherein the curved track part includes a front sloped region and a rear sloped region.

* * * * *

UNITED STATES PATENT AND TRADEMARK OFFICE
CERTIFICATE OF CORRECTION

| | |
|---|---|
| PATENT NO. | : 10,926,128 B2 |
| APPLICATION NO. | : 16/206847 |
| DATED | : February 23, 2021 |
| INVENTOR(S) | : Seon Kyung Yoo et al. |

Page 1 of 1

It is certified that error appears in the above-identified patent and that said Letters Patent is hereby corrected as shown below:

On the Title Page

In Column 1, item (54), Title, Line 1, delete "EXCERCISE" and insert -- EXERCISE --.

In the Specification

In Column 1, Line 1, delete "EXCERCISE" and insert -- EXERCISE --.

In Column 3, Line 2, delete "tree" and insert -- free --.

In Column 9, Line 56, delete "embodiment" and insert -- embodiment. --.

In the Claims

In Column 11, Line 27, Claim 8, delete "user s" and insert -- user's --.

In Column 11, Line 29 (approx.), Claim 9, delete "unit configured receive an input," and insert -- unit configured to receive an input --.

In Column 12, Line 35 (approx.), Claim 9, delete "treadmill," and insert -- treadmill; --.

In Column 12, Line 40 (approx.), Claim 9, after "(V1)" insert -- being --.

Signed and Sealed this
Tenth Day of August, 2021

Drew Hirshfeld
*Performing the Functions and Duties of the*
*Under Secretary of Commerce for Intellectual Property and*
*Director of the United States Patent and Trademark Office*